(12) United States Patent
Moliner et al.

(10) Patent No.: US 7,521,571 B2
(45) Date of Patent: Apr. 21, 2009

(54) DISULFIDE, SULFIDE, SULFOXIDE, AND SULFONE DERIVATIVES OF CYCLIC SUGARS AND USES

(75) Inventors: Jose Repolles Moliner, Barcelona (ES); Eduardo Salas Perez-Rasilla, Barcelona (ES); Francisco Pubill Coy, Barcelona (ES)

(73) Assignee: Lacer, Barcelona (ES)

( * ) Notice: Subject to any disclaimer, the term of this patent is extended or adjusted under 35 U.S.C. 154(b) by 72 days.

(21) Appl. No.: 10/544,237

(22) PCT Filed: Sep. 29, 2004

(86) PCT No.: PCT/EP2004/010882

§ 371 (c)(1),
(2), (4) Date: Jun. 5, 2006

(87) PCT Pub. No.: WO2005/037842

PCT Pub. Date: Apr. 28, 2005

(65) Prior Publication Data

US 2006/0235052 A1    Oct. 19, 2006

(30) Foreign Application Priority Data

Oct. 3, 2003    (ES)    ............................. 200302368

(51) Int. Cl.
C07D 493/00    (2006.01)
(52) U.S. Cl. .................................................... 549/464
(58) Field of Classification Search ............. 549/464
See application file for complete search history.

(56) References Cited

U.S. PATENT DOCUMENTS

| | | | |
|---|---|---|---|
| 3,886,186 A | 5/1975 | Dvonch et al. | |
| 4,371,703 A | 2/1983 | Stoss | |
| 4,891,373 A * | 1/1990 | Stoss et al. ............... | 514/228.2 |
| 5,665,766 A * | 9/1997 | Byrne et al. ................ | 514/470 |
| 6,858,632 B2 * | 2/2005 | Moliner et al. .............. | 514/338 |
| 2002/0013483 A1 | 1/2002 | Brader et al. | |

FOREIGN PATENT DOCUMENTS

| | | |
|---|---|---|
| AU | 21345/95 | 3/1995 |
| CN | 1322205 A | 11/2001 |
| EP | 0 290 885 | 11/1988 |
| EP | 0 530 887 A1 | 3/1993 |
| EP | 1 120 419 A1 | 8/2001 |
| ES | 2 142 773 | 4/2000 |
| ES | 2142773 A1 * | 4/2000 |
| FR | 2 134 698 | 12/1972 |
| RU | 96121403 | 10/1996 |
| WO | WO 93/03037 * | 2/1993 |
| WO | WO 00/20420 | 4/2000 |

OTHER PUBLICATIONS

Caveda L. et al., "Inhibition of Cultured Cell Growth by Vascular Endothelial Cadherin (Cadherin-5/VE-Cadherin)", *J. Clin. Invest.*, 98(4):886-893 (1996).
Del Maschio A. et al., "Polymorphonuclear Leukocyte Adhesion Triggers the Disorganization of Endothelial Cell-to-Cell Adherens Junctions", *The Journal of Cell Biology*, 135(2):497-510 (1996).
Furchgott R., "Bioassays with Isolated Vascular Tissue for Endothelium-Derived Relaxing Factor, Nitric Oxide and Nitric Oxide Donors", *Feelisch & Stamler, eds., John Wiley & Sons*, pp. 567-581 (1996).
Nallet J.P. et al., "Synthesis of a Series of Hexitol and Aminodeoxyhexitol Mononitrate Derivatives Containing a Sulfur Group and Pharmacological Evaluation on Isolated Rat Aortas", *Eur. J. Org. Chem.*, 933-943 (1998).
Hirata Y. et al., "Effect of JTV-506, a Novel Vasodilator, on Experimental Angina Model in Rats", *Journal of Cardiovascular Pharmacology*, 31(2):322-326 (1998).
Spranger T. et al., "How Different Constituents of Human Plasma and Low Density Lipoprotein Determine Plasma Oxidizability by Copper", *Chemistry and Physics of Lipids*, 91:39-52 (1998).
Feuerstein G.Z. et al., "Antithrombotic Efficacy of a Novel Murine Antihuman Factor IX Antibody in Rats", *Arterioscler Thromb Vasc Biol.*, 19:2554-2562 (1999).
Shore B. et al., "Rabbits as a Model for the Study of Hyperlipoproteinemia and Atherosclerosis", *Day CE (ed) Atherosclerosis Drug Discovery* 123-141 (1976).
De Lucchi O., "Chemoselective Reduction of Isosorbide-2,5-Dinitrate", *Gazzetta Chimica Italianoa, Societa Chimica*, 117(3):173-176 (1987), XP-000984806.
Kurz K.D. et al., "Rat Model of Arterial Thrombosis Induced by Ferric Chloride", *Thrombosis Research*, 60(4):269-280 (1990).

(Continued)

*Primary Examiner*—D. Margaret Seaman
*Assistant Examiner*—Nizal S Chandrakumar
(74) *Attorney, Agent, or Firm*—Scully, Scott, Murphy & Presser, P.C.

(57) ABSTRACT

In the present invention there are disclosed new derivatives of dianhydrohexite mononitrate corresponding to formula (I), tautomers, pharmaceutically acceptable salts, prodrugs and solvates thereof as well as pharmaceutical compositions comprising these compounds and uses thereof.

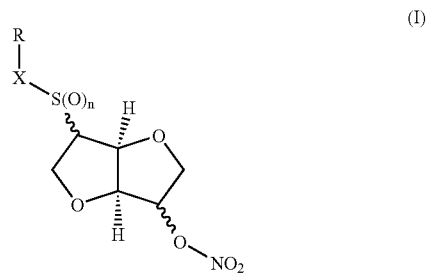

(I)

9 Claims, No Drawings

OTHER PUBLICATIONS

Stephan Z.F. et al., "Rapid Fluorometric Assay of LDL Receptor Activity by Dil-Labeled LDL", *Journal of Lipid Research*, 34:325-330 (1993).

Salas E. et al., "Endothelium-Independent Relaxation by 17-α-Estradiol of Pig Coronary Arteries", *European Journal of Pharmacology*, 258:47-55 (1994).

Trongvanichnam K. et al., "Effects of Chronic Oral Administration of Isosorbide Dinitrate on In Vitro Contractility of Rat Arterial Smooth Muscle", *Jpn. J. Pharmacol.*, 71:167-173 (1996).

Bombeli T. et al., "Endothelial Cells Undergoing Apoptosis Become Proadhesive for Nonactivated Platelets", *Blood*, 93(11):3831-3838 (1999).

Martín-Satué M. et al., "Overexpression of α(1,3)-Fucosyltransferase VII is Sufficient for the Acquisition of Lung Colonization Phenotype in Human Lung Adenocarcinoma HAL-24Luc Cells", *British Journal of Cancer*, 80(8):1169-1174 (1999).

Lynch S.M. et al., "Plasma Thiols Inhibit Hemin-Dependent Oxidation of Human Low-Density Lipoprotein", *Biochimica et Biophysica Acta*, 1485:11-22 (2000).

Pedreño J. et al., "Molecular Requirements in the Recognition of Low-Density Lipoproteins (LDL) by Specific Platelet Membrane Receptors", *Thrombosis Research*, 99:51-60 (2000).

Colomé C. et al., "Small Oxidative Changes in Atherogenic LDL Concentrations Irreversibly Regulate Adhesiveness of Human Endothelial Cells: Effect of the Lazaroid U74500A", *Atherosclerosis*, 149:295-302 (2000).

Pedreño J. et al., "Low-Density Lipoprotein (LDL) Binds to a G-Protein Coupled Receptor in Human Platelets, Evidence that the Proaggregatory Effect Induced by LDL is Modulated by Down-Regulation of Binding Sites and Desensitization of its Mediated Signaling", *Atherosclerosis*, 155:99-112 (2001).

Excerpt from the Orange Book, Record Search Query on "020225" (2005).

Excerpt from the Orange Book, Record Search Query on "020215" (2005).

"Isosorbide Mononitrate", Information from Answers.com (2005).

Part of a document referred to as "Myocardial Heart Attack", http://www.mailxmail.com/curso/vida/infartomiocardio/capitulo6.htm (2005).

"Monoket® Tablets", *Schwarz Pharma*, PC3734A (1999).

Ukraine Patent Application No. 00063467 A, dated Jan. 15, 2004 (abstract).

Translation of Georgian Search Report dated Jul. 13, 2007.

* cited by examiner

DISULFIDE, SULFIDE, SULFOXIDE, AND SULFONE DERIVATIVES OF CYCLIC SUGARS AND USES

FIELD OF THE INVENTION

The present invention relates to disulfide, sulfide, sulfoxide, and sulfone derivatives of 1,4:3,6-dianhydrohexite mononitrate and their use for the prevention and/or treatment of vascular disorders.

TECHNICAL BACKGROUND

Nitric oxide (NO) is one of the smallest and simplest of the biologically active molecules in nature. Moreover, NO appears to be one of the most ubiquitous molecules in mammalian species. As one of the most widespread signalling molecules, NO is a major player in controlling nearly every cellular and organ function in the body. NO is the only endogenous molecule able to function as a neurotransmitter, autacoid, constitutive mediator, inducible mediator, cytoprotective molecule, and cytotoxic molecule.

Because NO plays multiple physiological roles in regulating numerous and diverse organ functions, defects in the NO pathway lead to the development of many different pathological conditions. These disorders include hypertension, atherosclerosis, coronary artery diseases, cardiac failure, pulmonary hypertension, stroke, impotence, vascular complications in diabetes mellitus, gastrointestinal ulcers, asthma, and other central- and systemic-nervous system disorders.

All nitric oxide donors (NODs) share the common property of producing NO-related activity when applied in biological systems and thus mimic endogenous NO responses. However, the pathways leading to NO formation/release differ significantly among the compound classes, as do their chemical reactivities. Whereas some compounds require enzymatic catalysis, others produce NO non-enzymatically. In some compounds, the liberation of NO is preceded by a reduction or an oxidation. The process is complicated still more by the specific susceptibility of compounds to the changes in pH, oxygen, light and temperature and by the different by-product formation that takes place during the decomposition or the metabolism. In addition, the kinetics of NO release from a given compound is often more important than the absolute amount of NO released. Moreover, the tissue distribution of the NODs and the site where NO is generated is also of great importance. All these considerations are important since they explain the very different pharmacological profiles obtained with the different NODs described in the literature and make it necessary to fully characterize the pharmacological profile of newly developed NODs in research and development.

Pharmaceutically useful NODs having a isosorbide-mononitrate skeleton are disclosed in WO 00/20420. The compounds as such disclosed therein do not form part of the present invention. That application describes organic nitrates capable of providing a potent vasodilating effect and which at the same time show a small or null tolerance effect. However, no indication exists for the possible use of said compounds for the treatment of platelet activation; thrombosis; stroke; tissue damage due to ischemia and/or to ischemia/reperfusion; pathological conditions where oxidative stress plays an important role in their pathogenesis; and/or atherosclerosis. Accordingly the new use of said compounds forms part of the present invention.

One of the principal problems of the nitrated organic compounds described in the literature and those used clinically resides in the fact that their mechanism of action is the relaxation of vascular smooth muscle without modifying other pathologic processes involved in cardiovascular diseases.

Tissue ischemia results in the depletion of intracellular adenosine triphosphate (ATP) stores, which subsequently compromises the function of membrane-associated, ATP-dependent ionic pumps in endothelial cells. This membrane dysfunction allows entry of calcium, sodium, and water into the cells. The resultant accumulation of calcium and other ions in the cell can result in cell swelling and the inappropriate activation of cellular enzymes. One enzyme that is activated by the rise in intracellular calcium during ischemia is xanthine dehydrogenase (XDH). Under normal conditions, hypoxanthine (a breakdown product of ATP metabolism) is oxidized by XDH, in an NADPH-dependent manner, to produce xanthine and uric acid. However, during the hypoxic condition of ischemia, hypoxanthine levels rise within the cell due to ATP hydrolysis, and there is a calcium-dependent activation of proteases that convert the NADPH-reducing XDH to an oxygen-reducing form of the enzyme, namely, xanthine oxidase (XO). On restoration of blood flow (reperfusion) to the tissue and with the reintroduction of molecular oxygen, XO will convert hypoxanthine to xanthine and uric acid, and it will catalyze the reduction of molecular oxygen to form both superoxide anion radicals ($O_2^-$) and hydrogen peroxide ($H_2O_2$). This XO-dependent mechanism of oxygen radical production has been invoked to explain the involvement of $O_2^-$ and $H_2O_2$ in reperfusion injury to a variety of organs, including intestine, brain, heart, and skeletal muscle.

The generation of oxygen radicals in postischemic tissues appears to overcome the capacity of endogenous antioxidants such as superoxide dismutase (SOD), catalase, glutathione to protect endothelial and parenchymal cells. Exogenous antioxidants such as SOD and catalase have been shown to attenuate the leukocyte infiltration and tissue injury elicited by ischemia and reperfusion.

Nitric oxide bioavailability appears to be reduced in reperfusion, which is likely due to a decline in endothelial NO production and an increased inactivation of NO by endothelial-cell-derived $O_2^-$. The limited bioavailability of NO contribute to the abnormal cell-cell interactions and vascular dysfunction during reperfusion. Nitric oxide-donating compounds have shown promise as protective agents in experimental models of ischemia-reperfusion. However, considering the processes involved in the damage by ischemia-reperfusion it would be of great interest to have a molecule with both properties: being a NO-donor and at the same time with antioxidant properties.

Atherosclerosis is an active process initiated by a continuous damage of the vascular endothelium. The view of atherosclerosis as a response to a damage of the endothelium was developed when the association of atherosclerosis with risk factors (high LDL plasma levels, low HDL plasma levels, hypertension, oxidative stress, tobacco consumption, diabetes mellitus, high Lp(a) plasma levels or modification of LDL such as oxidation or glycation that prevent LDL removal by the specific receptors) was studied. LDL accumulates in the vascular wall as a consequence of a vascular-endothelial cells active transport. During this process, the LDL suffers the oxidation of a part of the molecule. The presence of oxidated-LDL (ox-LDL) is of capital importance in the development of the atherosclerotic lesion. To the same extent, the theory that oxidized LDL is responsible for some of the pathological features of atherosclerotic lesions derives from the findings in cultured cells systems that oxidized LDL causes cellular changes that correlate with known aspects of arterial lesions but are not induced by native LDL. Endothelial injury, LDL retention in intimal interstitium, monocyte recruitment into intima, engorgement of macrophages with lipoprotein-derived lipid, smooth muscle cell migration and proliferation, accumulation of necrotic cell debris, and tendencies towards vasoconstriction and procoagulant activity are characteristics of atherosclerosis.

Cardiac allograft vasculopathy is an unusually accelerated and diffuse form of coronary atherosclerosis that limits the long-term success of cardiac transplantation. Coronary endothelial vasodilator dysfunction is a common and early marker for the development of cardiac allograft vasculopathy.

Accordingly, novel nitrated organic compounds which, in addition to the vasodilating activity, could combine activities that would allow them to modify other pathologic processes involved in cardiovascular diseases, such as atherosclerosis and tissue damage due to ischemia and/or due to ischemia and reperfusion, will represent an important advantage with respect to the compounds nowadays in use.

SUMMARY OF THE INVENTION

An object of the invention is a novel type of compounds, derivatives of dianhydrohexite mononitrate, which are capable of providing a potent vasodilating effect and which at the same time modify other pathologic processes involved in cardiovascular diseases such as, atherosclerosis, cardiac allograft vasculopathy, and tissue damage due to ischemia and/or to ischemia-reperfusion.

Another object of the invention is a novel type of compounds, derivatives of dianhydrohexite mononitrate, which are capable of providing a potent antithrombotic effect even at a dose that does not modify the blood pressure.

Another object of the invention is a novel type of compounds, derivatives of dianhydrohexite mononitrate, which are capable of providing a synergistic effect with thrombolytic drugs, anticoagulants, antithrombotics, antioxidants and hypolipemiant drugs.

A further object of the present invention relates to the new use of derivatives of dianhydrohexite mononitrate for the manufacture of a pharmaceutical composition for the treatment of cardiovascular disorders related to atherosclerosis.

DETAILED DESCRIPTION OF THE INVENTION

It is an object of the present invention to provide a compound according to formula (I), or a tautomer, a pharmaceutically acceptable salt, a prodrug or a solvate thereof:

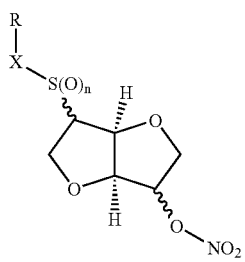

(I)

wherein:
n is an integer of 0, 1, or 2,
X represents —S(O)$_m$—, —(C═O)— or a single bond, wherein m is an integer of 0, 1, or 2; with the proviso that when X represents —(C═O)— then n is 0,
R represents hydrogen or is a residue R$^a$, which residue R$^a$ is selected from the group consisting of:

$C_{1-6}$ alkyl;
$C_{2-6}$ alkenyl;
$C_{3-8}$ cycloalkyl;
$C_{3-8}$ cycloalkyl, wherein one $CH_2$ group is replaced by O, S, NH or $NCH_3$;
$C_{4-8}$ cycloalkenyl;
$C_{4-8}$ cycloalkenyl, wherein one $CH_2$ group is replaced by O, S, NH or $NCH_3$;
phenyl;
pyridyl;
thiophenyl;
nitrosyl;
S-cysteinyl;
S-glutathionyl; and

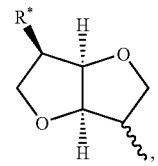

wherein R* is selected from the group consisting of hydrogen, $C_{1-6}$ alkyl, $C_{2-6}$ alkenyl, $C_{3-8}$ cycloalkyl, $C_{4-8}$ cycloalkenyl, acetyloxy, hydroxyl, $ONO_2$ and halogen,
wherein R$^a$ optionally is substituted by one to three groups independently selected from $C_{1-6}$ alkyl, $C_{2-6}$ alkenyl, $C_{3-8}$ cycloalkyl, $C_{4-8}$ cycloalkenyl, acetyloxy, hydroxyl, $ONO_2$ and halogen.

It is preferred in the compounds according to formula (I) when RXS(O)$_n$— and —$ONO_2$ are trans to each other with respect to the ring plane, as depicted in formulae (Ia) and (Ib):

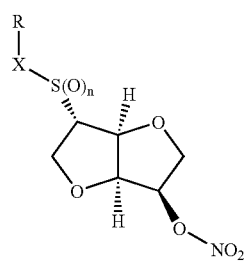

(Ia)

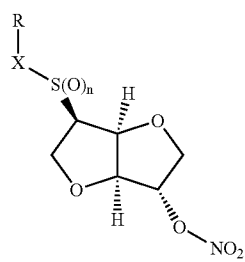

(Ib)

that then RXS(O)$_n$— does not represent

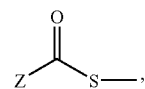

wherein Z is an $C_1$-$C_4$ alkyl group, aryl group, or an aralkyl group.

Surprisingly, in addition to the potent vasodilating effect with small or null tolerance, the compounds of formula (I) possess anti platelet activation, anti thrombotic, anti stroke, anti oxidant, anti tissue injury/damage due to ischemia and/or ischemia/reperfusion, and anti atherosclerotic properties.

Another embodiment of the present invention relates to a pharmaceutical composition comprising as active ingredient at least one of the derivatives of dianhydrohexite mononitrate according to formula (I), a tautomer, a pharmaceutically acceptable salt, a prodrug or a solvate thereof.

A further embodiment of the present invention relates to the use of at least one derivative of dianhydrohexite mononitrate according to formula (I), a tautomer, a pharmaceutically acceptable salt, a prodrug or a solvate thereof as active ingredient for the manufacture of a pharmaceutical composition for the prevention and/or treatment of atherosclerosis, endothelial dysfunctions, vasospasm, cardiac allograft vasculopathy, dysfunctions of the circulatory system, platelet activation, thrombosis, stroke, pathological conditions where oxidative stress plays an important role in their pathogenesis such as but not limited to Alzheimer's disease, pathological conditions where a deficit of nitric oxide plays an important role in their pathogenesis, and/or tissue damage due to ischemia and/or due to ischemia-reperfusion.

The above used expressions will be outlined in more detail below:

The expression "pharmaceutically acceptable salt, solvate or prodrug thereof" describes any pharmaceutically acceptable salt, ester, solvate or any other compound that, administered to a patient (directly or indirectly), provides a compound described herein. Nevertheless, it will be considered that the pharmaceutically non acceptable salts also are included within the limits of this invention since these compounds can be useful in the preparation of pharmaceutically acceptable salts. Preparation of salts, prodrugs and derivatives can be carried out by methods known in the state of the art.

For example, pharmaceutically acceptable salts of compounds described herein are synthesized from the corresponding compound, that contains an acid or basic group, by conventional chemical methods. Generally, these salts are, for example, prepared by means of the reaction of free acidic or basic forms of these compounds in a stoichiometric amount with a corresponding base or acid in water or an organic dissolvent or a mixture of both. Non-aqueous media like ether, ethyl acetate, isopropanol or acetonitrile are generally preferred. Examples of acid salts include mineral acid salts such as hydrochloride, hydrobromide, hydriodide, sulphate, nitrate, phosphate and organic acid salts such as acetate, maleate, fumarate, citrate, oxalate, succinate, tartrate, mandelate, methylsulphonate and p-toluensulphonate.

Examples of basic salts include inorganic salts such as salts of sodium, potassium, calcium, ammonium, magnesium, aluminium and lithium, and organic salts such as ethylenediamine, ethanolamine, N,N-dialkyleneethanolamine, triethanolamine, glucamine and basic salts of amino acids.

The particularly preferred derivatives or prodrugs are those that increase the bioavailability of compounds of the present invention when such compounds are administered to a patient (for example, allowing that an administered compound of oral form more quickly is absorbed in blood) or those that increase the liberation of the corresponding compound to a biological compartment (for example, the brain or the lymphatic system).

Any compound that is a prodrug of a compound of formula (I) belongs to the scope of the invention. The term "prodrug" is used in the amplest sense and includes derivatives that "in vivo" are metabolized into compounds of the invention. Such derivatives include, depending on the present functional groups in the molecule and without limitation, the following derivatives: esters, esters of amino acids, phosphate esters, metallic salts of sulfonated compounds, carbamates and amide esters.

The compounds of the present invention can preferably be in their crystalline form, or like free compounds or solvates. The salvation methods which can be applied are those generally known in the art. The suitable solvates are pharmaceutically acceptable solvates. It is preferred that the solvate is a hydrate.

It is preferred that the compounds of formula (I), or their salts or solvates are in their acceptable pharmaceutically substantially pure form. By pharmaceutically acceptable form it is understood, "inter alia", having an pharmaceutically acceptable level of purity excluding usual pharmaceutical additives such as diluents and carriers, and including material considered non-toxic at levels of normal doses. The levels of purity for the drug are over 50%, preferably over 70% and still more preferable over 90%. In an even more preferred embodiment the compounds of formula (I), or the salts, solvates or prodrugs thereof have purity over 95%.

The compounds of the present invention represented by the formula (I) can include enantiomers, depending on the presence of chiral or isomeric centers, and/or depending on the presence of multiple bonds (for example, Z, E). The pure isomers, enantiomers or diastereoisomers and their mixtures are within the scope of the present invention.

The term "halogen" refers to fluorine, chlorine, bromine, or iodine, whereof bromine is preferred.

The term "$C_{1-6}$ alkyl" as used herein refers to a straight or branched chain alkyl moiety having from 1 to 6 carbon atoms, including for example, methyl, ethyl, n-propyl, isopropyl, n-butyl, iso-butyl, sec-butyl, t-butyl, pentyl, and hexyl.

The term "$C_{2-6}$ alkenyl" as used herein refers to a straight or branched chain alkenyl moiety having from 2 to 6 carbon atoms and at least one double bond of either E or Z stereochemistry where applicable. This term would include, for example, vinyl, allyl, 1- and 2-butenyl, and 2-methyl-2-propenyl.

The term "$C_{3-8}$ cycloalkyl" as used herein refers to an alicyclic group having from 3 to 8 carbon atoms. Some illustrative examples of such cycloalkyl groups are cyclopropyl, cyclobutyl, cyclopentyl and cyclohexyl.

Accordingly, the term "$C_{3-8}$ cycloalkyl wherein one $CH_2$ group is replaced by O, S, NH or $NCH_3$" refers to an alicyclic group having from 3 to 8 carbon atoms wherein one $CH_2$ group is replaced by O, S, NH or $NCH_3$. Some illustrative examples of such groups are tetrahydropyrane, tetrahydrofurane, pyrrolidine, piperidine, and tetrahydrothiophene.

The term "$C_{4-8}$ cycloalkenyl" refers to an alicyclic group having from 4 to 8 carbon atoms. Some illustrative examples of such cycloalkenyl groups are cyclopentenyl, cyclohexenyl, cycloheptenyl and cyclooctenyl.

It is preferred that R represents hydrogen, $C_{1-6}$ alkyl, $C_{2-6}$ alkenyl, $C_{3-8}$ cycloalkyl, $C_{4-8}$ cycloalkenyl, ($C_{1-6}$ alkyl) $C_{3-8}$ cycloalkyl, ($C_{1-6}$ alkyl) $C_{4-8}$ cycloalkenyl, phenyl or ($C_{1-6}$ alkyl)phenyl, whereas $C_{1-6}$ alkyl is especially preferred.

It is further preferred that in formula (I) either one or both of m and n is 0.

Also it is-preferred that X represents a single bond or —S—.

It is especially preferred that the compounds of formula (I) correspond to compounds which are represented by formula (Ia) and/or formula (Ib):

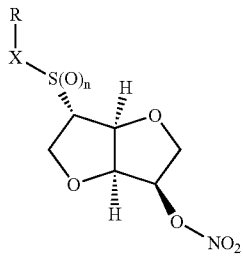
(Ia)

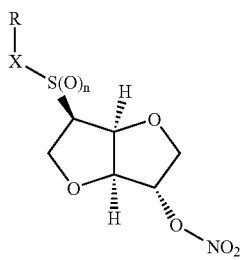
(Ib)

The compounds of formula (I) also include (R) and (S) diastereoisomers according to the formulas (Ic) and (Id):

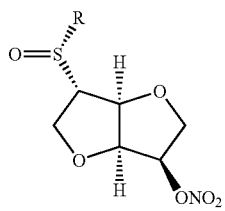
(Ic)

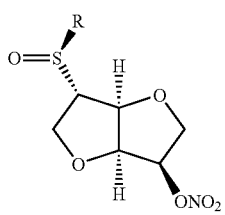
(Id)

Especially preferred compounds of formula (I) are:
2-thioisosorbide 5-mononitrate,
5,5'-dinitrato-2,2'-dithiodiisosorbide,
2-methylthioisosorbide 5-mononitrate,
2-[(R)-methylsulfinyl]isosorbide 5-mononitrate,
2-[(S)-methylsulfinyl]isosorbide 5-mononitrate,
2-methyl-sulfinylisosorbide 5-mononitrate,
2-methylsulfonylisosorbide 5-mononitrate,
S-nitroso-2-thioisosorbide 5-mononitrate,
2-(tetrahydropyran-2-yl-thio)isosorbide 5-mononitrate,
2-(isosorbidyl-2'-dithio)isosorbide 5-mononitrate, and
2-(5'-acetyloxyisosorbidyl-2'-dithio)isosorbide 5-mononitrate.

Further, it is especially preferred to use 2-acetylthio-isosorbide-5-mononitrate (compound (12)), a tautomer, a pharmaceutically acceptable salt, a prodrug and/or a solvate thereof:

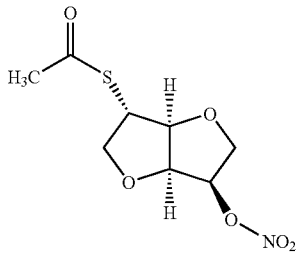
12 as active ingredient for the manufacture of a pharmaceutical composition for the prevention and/or treatment of thrombosis, ischemia, cell/tissue damage induced by ischemia and/or by ischemia and reperfusion, hypertension, vasospasm, atherosclerosis and/or cardiac graft vasculopathy.

Additionally, the compounds of formula (I), especially 2-acetylthioisosorbide 5-mononitrate (12), their tautomers, pharmaceutically acceptable salts, prodrugs and solvates thereof, may also be used in a therapy for the prevention and/or treatment of atherosclerosis, cardiac allograft vasculopathy, platelet activation, thrombosis, stroke, pathological conditions where oxidative stress plays an important role in their pathogenesis, and/or tissue damage due to ischemia and/or due to ischemia-reperfusion. These compounds may especially be used in the prevention and/or treatment of pathological conditions, where oxidative stress plays an important role in their pathogenesis, such as allergy, stroke, Alzheimer's disease, and/or ischemic cardiovascular diseases. The pharmaceutical compositions may be administered by different routes. For example, they may be administered orally in form of pharmaceutically preparations such as tablets, capsules, syrups and suspensions. Parenterally in form of solutions or emulsions, etc. They may also be administered topically in form of creams, pomades, balsams, etc., and transdermically for example through the use of patches or bandages. They may also be applied directly in the rectum as suppositories. The preparations may comprise physiologically acceptable carriers, excipients, activators, chelating agents, stabilizers, etc. In case of injections there may be incorporated physiologically acceptable buffers, solubilizing agents or isotonics.

The pharmaceutical compositions according to the present invention may further comprise a thrombolytic agent, preferably plasminogen activator, urokinase, streptokinase, alteplase or anistreplase. They may also contain an anticoagulant agent, preferably heparin, dicoumarol, acenocoumarol, enoxaparine or pentosan polysulfate. Moreover, they may contain additionally an antithrombotic agent preferably acetyl salicylic acid, dipyridamole, ticlopidine, clopidrogel, triflusal, pentosan polysulfate or abciximab. They can further comprise an immunoglobulin or fragment thereof having a specificity for glycoprotein IIb/IIIa.

Alternately, the pharmaceutical compositions according to the invention may further comprise an hypolipemiant agent preferably simvastatin, lovastatin, atorvastatin, pravastatin, fluvastatin, eptastatin, lifibrol, acifran, acitemate, glunicate or rosuvastatine. They may also contain an antioxidant/free radical scavengers agent, preferably selected from nicaraven, ranolazine, emoxipin, glutatione, edaravone, raxofelast, lycopene, N-acetyl-L-cysteine, N-acetyl-D-cysteine, a racemic mixture of N-acetyl-L-cysteine and N-acetyl-D-cysteine, or carvedilol.

The pharmaceutical compositions according to the present invention may be used for the treatment and/or prevention of atherosclerosis, cardiac allograft vasculopathy, platelet activation, thrombosis, stroke, tissue damage due to ischemia and/or due to ischemia-reperfusion, and/or pathological conditions where oxidative stress plays an important role in their pathogenesis (such as but not limited to allergy, stroke, Alzheimer's disease, ischemic cardiovascular diseases); and/or pathological conditions where a deficit of NO plays an important role in their pathogenesis. They can also be used for the treatment and/or prevention of dysfunctions of the circulatory system preferably cardiovascular and coronary dysfunctions.

The daily dose may be varied depending on the specific symptoms, the age, the body weight of the patients, the specific mode of administration, etc., and a daily normal dose for an adult person could be between 0.1 to 500 mg, and could be administered as one dose only or divided into several doses during the day.

The compounds of the present invention can be prepared by preparation methods known in the art, by adaptation of the known processes by the skilled person or by a new process described below.

Hence, another embodiment of the present invention relates to a processes for preparing compounds of formula (I), tautomers, pharmaceutically acceptable salts, prodrugs and solvates thereof.

According to the invention it is preferable to prepare a compound of the formula (I), a tautomer, a pharmaceutically acceptable salt, a prodrug or a solvate thereof by the process outlined below:

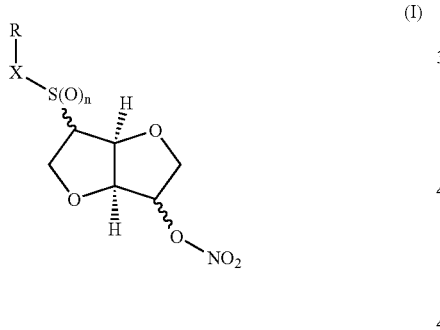

(I)

wherein:
n is an integer of 0, 1, or 2,
X represents —S(O)$_m$— or a single bond, wherein m is an integer of 0, 1, or 2,
and R represents hydrogen or is a residue R$^a$, which residue R$^a$ is selected from the group consisting of:
C$_{1-6}$ alkyl;
C$_{2-6}$ alkenyl;
C$_{3-8}$ cycloalkyl;
C$_{3-8}$ cycloalkyl, wherein one CH$_2$ group is replaced by O, S, NH or NCH$_3$;
C$_{4-8}$ cycloalkenyl;
C$_{4-8}$ cycloalkenyl, wherein one CH$_2$ group is replaced by O, S, NH or NCH$_3$;
phenyl;
pyridyl;
thiophenyl;
nitrosyl;
S-cysteinyl;
S-glutathionyl; and

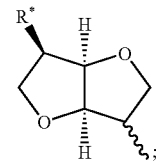

wherein R* is selected from the group consisting of hydrogen, C$_{1-6}$ alkyl, C$_{2-6}$ alkenyl, C$_{3-8}$ cycloalkyl, C$_{4-8}$ cycloalkenyl, acetyloxy, hydroxyl, ONO$_2$ and halogen, wherein R$^a$ optionally is substituted by one to three groups independently selected from the group consisting of C$_{1-6}$ alkyl, C$_{2-6}$ alkenyl, C$_{3-8}$ cycloalkyl, C$_{4-8}$ cycloalkenyl, acetyloxy, hydroxyl, ONO$_2$ and halogen, which process comprises conducting the following steps:
a) effecting the hydrolysis of a compound of formula (IIa):

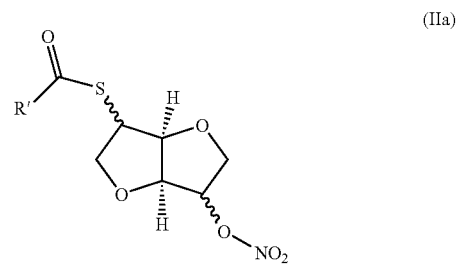

(IIa)

wherein R' is C$_1$-C$_6$ alkyl, preferably methyl, to obtain the following compound:

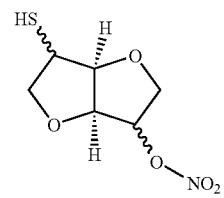

and
(b) optionally, effecting on the compound prepared according to the step (a):
I. an oxidation reaction to obtain:

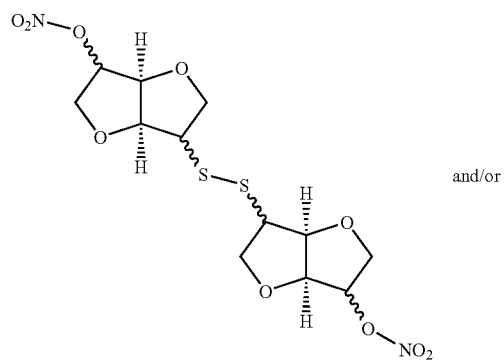

and/or

-continued

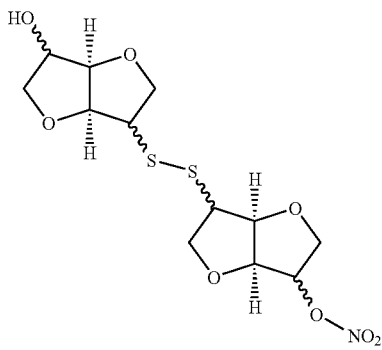

optionally followed by a second oxidation to obtain the following compound:

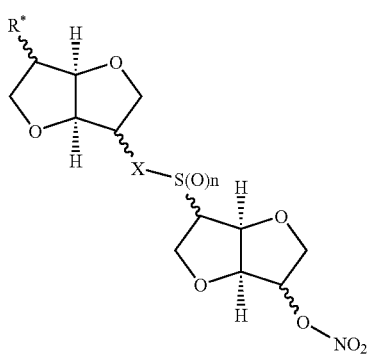

wherein:
n is 1 or 2,
X is —S(O)$_m$—, wherein m is 0, 1 or 2, and
R* represents hydroxyl or ONO$_2$;
II. a substitution reaction to obtain:
a compound according to formula (I), wherein:
n is an integer of 0,
X represents a bond,
and R does not represent nitrosyl,
optionally followed by an oxidation to obtain a compound according to formula (I), wherein:
n is an integer of 0,
X represents —S(O)$_m$—, wherein m is an integer of 0 or 1,
and R does not represent nitrosyl;
III. a substitution reaction to obtain:
a compound according to formula (I), wherein:
n is an integer of 0, and
X represents —S—;
optionally followed by an oxidation to obtain a compound according to formula (I), wherein:
n is an integer of 1 or 2, and
X represents —S(O)$_m$—, wherein m is 0, 1 or 2; or
IV. a nitrosation reaction to obtain:

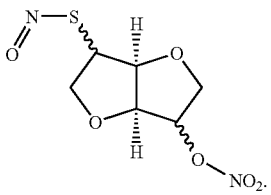

According to the above process of the invention it is especially preferable to prepare a compound of the formula (Ia), a tautomer, a pharmaceutically acceptable salt, a prodrug or a solvate thereof:

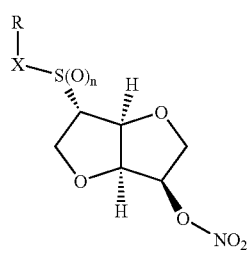

(Ia)

wherein n, X, m and R have the above meaning, and wherein said process comprises conducting the following steps:
a) effecting the hydrolysis of a compound of formula (II):

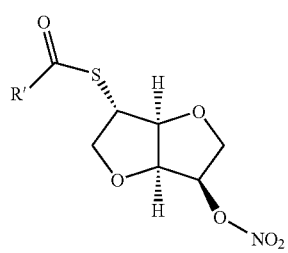

(II)

wherein R' is C$_1$-C$_6$ alkyl, preferably methyl, to obtain 2-thioisosorbide 5-mononitrate (1),

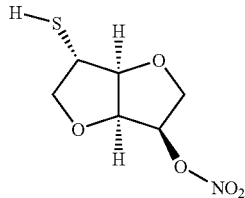

(1)

and
(b) optionally, effecting on compound (1) prepared according to the step (a):
I. an oxidation reaction to obtain:
5,5'-dinitrato-2,2'-dithiodiisosorbide (2) or 2-(isosorbidyl-2'-dithio) isosorbide 5-mononitrate (8), optionally followed by a second oxidation to obtain a compound according to formula (Ie):

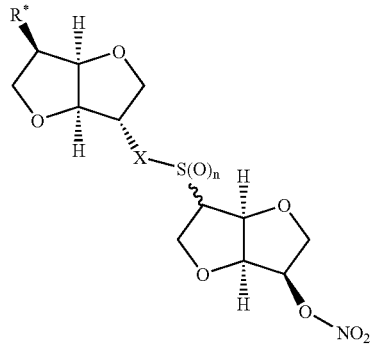

(Ie)

wherein:
n is 1 or 2,
X is —S(O)$_m$—, wherein m is 0, 1 or 2, and
R* represents hydroxyl or ONO$_2$;

II. a substitution reaction to obtain:
a compound according to formula (Ia), wherein:
n is an integer of 0,
X represents a bond,
and R does not represent nitrosyl,
optionally followed by an oxidation to obtain a compound according to formula (Ia), wherein:
n is an integer of 0,
X represents —S(O)$_m$—, wherein m is an integer of 0 or 1,
and R does not represent nitrosyl;

III. a substitution reaction to obtain:
a compound according to formula (Ia), wherein:
n is an integer of 0, and
X represents —S—;
optionally followed by an oxidation to obtain a compound according to formula (Ia), wherein:
n is an integer of 1 or 2, and
X represents —S(O)$_m$—, wherein m is 0, 1 or 2; or IV. a nitrosation reaction to obtain:
S-nitroso-2-thioisosorbide 5-mononitrate (6).

Optional step (b) of this new process of the invention is described schematically in Schemes 1 to 4 for specific compounds of the invention. These Schemes 1 to 4 relate to the oxidation reaction I, the substitution reaction II, the substitution reaction III, and the nitrosation reaction IV, respectively.

A specifically preferred process of the invention includes steps (a) and (b) II for the preparation of:
2-[(R)-alkylsulfinyl]isosorbide 5-mononitrate and/or
2-[(S)-alkylsulfinyl]isosorbide 5-mononitrate.

It is further preferred that both diastereoisomers are separated subsequently, which separation may be carried out by using conventional methods known in the art.

A further preferred preparation process of the invention concerns the preparation of a compound of formula (11) or a tautomer, a pharmaceutically acceptable salt, a prodrug or a solvate thereof:

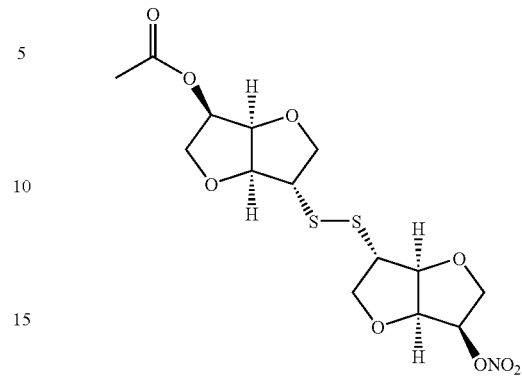

(11)

which process comprises the following steps:
a) effecting an oxidation reaction of a compound of formula (III):

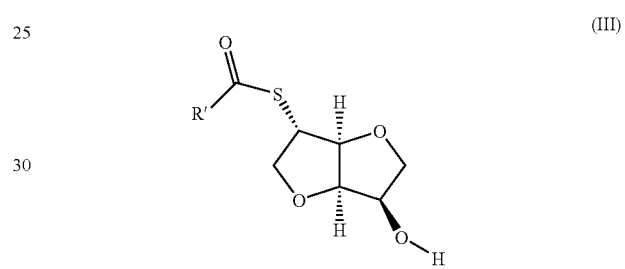

(III)

wherein R' is C$_1$-C$_6$ alkyl, preferably methyl, to obtain 2,2'-dithio-diisosorbide (10),

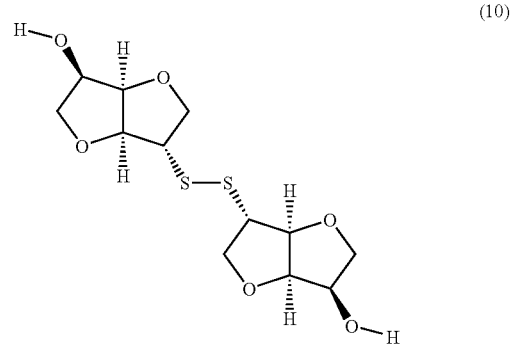

(10)

and
(b) effecting a nitration reaction of the compound prepared in step (a) with a nitrating agent in the presence of a carboxylic anhydride, preferably acetic anhydride.

Finally, another embodiment of the present invention relates to 2,2'-dithiodiisosorbide, compound (10), which is an intermediate compound in the preparation of compound (11) of the invention.

In the working examples herein (vide infra) there are described in detail suitable processes to obtain various of the compounds according to the general formula (I). In view of these examples, it is within the skilled persons general knowledge to obtain the compounds not explicitly exemplified herein via suitable modifications of the working examples herein. It will be apparent to the skilled person that these examples are solely for illustrative purposes and must not be considered to limit the invention.

EXAMPLES

The compounds obtained in the examples that appear below are identified by their proton ($^1$H-NMR) and carbon-13 ($^{13}$C-NMR) nuclear magnetic resonance spectroscopy data.

The nuclear magnetic resonance spectra were recorded with Varian Gemini-2000 or Varian Gemini-300 spectrometers.

The operating frequency and the solvent used to record the spectrum are indicated in the $^1$H-NMR spectra. The position of the signals is indicated in δ (ppm), with the signal of the solvent protons taken as the reference. The reference values were 7.24 ppm for deuterated chloroform and 2.49 ppm for deuterated dimethyl sulfoxide. The signal obtained from tetramethylsilane (TMS) protons is occasionally taken as an internal reference, with 0 ppm used as a reference value. The number of protons for each signal as measured by electronic integration and the type of signal are indicated in parentheses, using the following abbreviations: s (singlet), d (doublet), t (triplet), dd (doublet of doublets), ddd (doublet of doublet of doublets), bs (broad signal), cs (complex signal), s.a. $D_2O$ (simplifies upon deuteration), d.a. $D_2O$ (disappears upon deuteration).

The operating frequency and the solvent used in each spectrum are indicated in the $^{13}$C-NMR spectra. The position of the signals is indicated in δ (ppm), with the signal of the solvent carbons taken as the reference. The reference values are 77.00 ppm for deuterated chloroform and 39.50 ppm for hexadeuterated dimethyl sulfoxide.

In some cases, nuclear magnetic resonance experiments were also carried out using the pulse sequences APT (Attached Proton Test), HETCOR (Heteronuclear Chemical Shift Correlation) or COSY (Correlated Spectroscopy) as an aid to assignment.

In the experimental part the following abbreviations are used:

| | |
|---|---|
| AcOEt | ethyl acetate |
| AcOH | acetic acid |
| DMSO-$d_6$ | hexadeuterated dimethyl sulfoxide |
| EtOH | ethyl alcohol |
| EtOEt | ethyl ether |
| HPLC | high performance liquid chromatography |
| Hx | hexane |
| MeI | methyl iodide |
| MeOH | methyl alcohol |
| LC-(ApcI)MS | liquid chromatography-atmospheric pressure chemical ionization mass spectrometry |
| s.d. | standard deviation |
| s.e.m. | standard error of mean |
| THP | tetrahydropyranyl |

Example 1

Method to Obtain 2-thioisosorbide 5-mononitrate (1)

In a 50 mL flask, 1.00 g (4.02 mmol) of 2-acetylthioisosorbide 5-mononitrate (12) obtained according to WO 00/20420 were dissolved in a 20.0 mL of methyl alcohol. 10.0 mL of a 10% methanol solution of sodium hydroxide were added all at once. After rapidly covering and stirring for 1 min at room temperature (ca. 25° C.), 2.23 mL of concentrated hydrochloric acid were added all at once. It was stirred and concentrated until dryness, eliminating the solvent at reduced pressure at a temperature below 30° C.

The residue was suspended in chloroform. This chloroform solution was filtered and then dried over anhydrous magnesium sulfate. After filtering the solvent was eliminated at reduced pressure. It was dried at reduced pressure to obtain 0.83 g of an orange-yellow oil corresponding to the product of interest. Yield: 100%.

$^1$H-NMR (200 MHz, CDCl$_3$): 5.36-5.26 (1H, m, CHONO$_2$), 4.95 (1H, t, J=5.0 Hz, CHCHONO$_2$), 4.42 (1H, d, 4.8 Hz, CHCHS), 4.07 (1H, dd, J=4.6 Hz, J=4.4 Hz, H—CHCHS), 3.97 (1H, dd, J=5.64 Hz, J=2.5 Hz, H—CHCHONO$_2$), 3.87-3.76 (2H, cs, H—CHCHS, H—CHCHONO$_2$), 3.45-3.35 (1H, m, CHS), 1.77 (1H, d, J=8.6 Hz, SH).

$^{13}$C-NMR (50 MHz, CDCl$_3$): 91.21 (CHCHS), 81.22 (CHONO$_2$), 81.07 (CHCHONO$_2$), 76.15 (CH$_2$CHS), 69.26 (CH$_2$CHONO$_2$), 42.82 (CHS).

Example 2

Method to Obtain 5,5'-dinitrato-2,2'-dithiodiisosorbide (2)

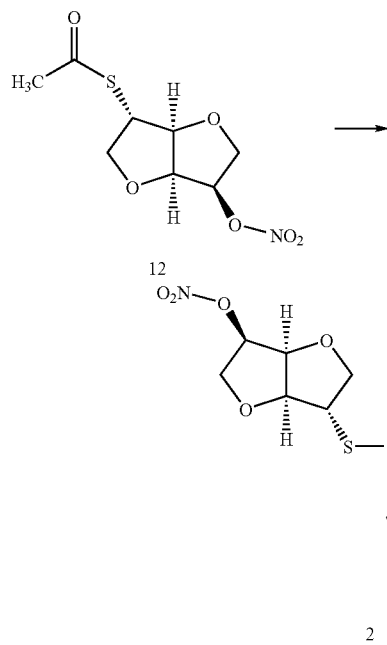

Procedure 1:

0.50 g of 2-acetylthioisosorbide 5-mononitrate (12) obtained alcohol. This solution was slowly added, drop by drop, to 200 mL of human plasma in a 250 mL flask with strong magnetic stirring. The reaction mixture was stirred at room temperature for 15 hours. The reaction crude was poured over 500.0 mL of acetonitrile while stirring vigorously, observing the instant precipitation of a flocculant white solid corresponding to the plasma proteins. It was centrifuged at 3000 rpm and at 20° C. for 30 min, the liquid separated and the solid (protein mass) suspended over 250.0 mL of acetonitrile. It was stirred and centrifuged under the same conditions as above (3000 rpm/20° C./30 min).

The supernatant liquor was decanted and combined with the previous one. The solvent was evaporated at reduced pressure at a temperature below 30° C. The resulting aqueous residue (about 200 mL) was extracted with 4×500 mL chloroform. The organic phases were combined and dried over anhydrous magnesium sulfate. After filtering the solvent was concentrated at reduced pressure. This results in 350 mg of a white solid which is purified by chromatography: (CHCl$_3$/AcOEt 6:1), isolating 250 mg of a white solid corresponding to the 2-thioisosorbide 5-mononitrate disulfide product (2). Yield: 60%.

Procedure 2:

In a 50 mL flask, 1.00 g (4.02 mmol) of 2-acetylthioisosorbide 5-mononitrate (12) obtained according to WO 00/20420 was dissolved in 20 mL of methyl alcohol and 10 mL of a 10% methanol solution of potassium hydroxide were added. The reaction mixture was covered and stirred for 5 hours at room temperature. The precipitation of a white solid corresponding to the disulfide (2) is observed during the reaction. The solid was filtered off and washed several times with methyl alcohol. Drying at reduced pressure, yields 0.58 g of a white solid corresponding to the 2-thioisosorbide 5-mononitrate disulfide product of interest (2). Yield: 70%.

$^1$H-NMR (200 MHz, DMSO-d$_6$): 5.51-5.43 (2H, m, 2CHONO$_2$), 4.96 (2H, t, J=5.4 Hz, 2CHCHONO$_2$), 4.51 (2H, d, J=4, 8 Hz, 2CHCHS), 4.04-3.73 (10H, cs, 2CH$_2$CHONO$_2$, 2CH$_2$CHS, 2CHS).

$^{13}$C-NMR (50 MHz, DMSO-d$_6$): 88.46 (2CHCHS), 83.31 (2CHONO$_2$), 81.50 (2CHCHONO$_2$), 73.24 (2 CH$_2$CHS), 69.95 (2CH$_2$CHONO$_2$), 54.01 (2CHS).

Example 3

Method to Obtain 2-methylthioisosorbide 5-mononitrate (3)

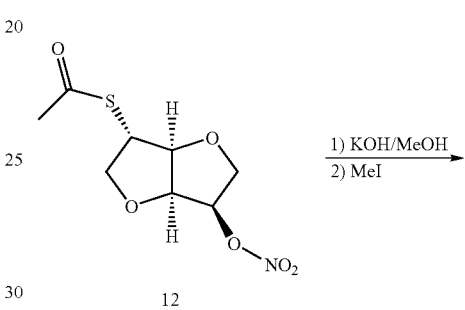

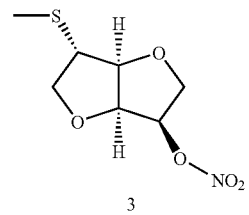

In a 50 mL flask, 1.00 g (4.02 mmol) of 2-acetylthioisosorbide 5-mononitrate (12) obtained according to WO 00/20420 were dissolved in 20.0 mL of methyl alcohol and 5.0 mL of a 10% methanol solution of potassium hydroxide was added all at once. The reaction mixture was covered and stirred for 5 minutes at room temperature. 2.0 mL of methyl iodide (32.00 mmol) were added all at once, the mixture covered and stirred for 2 hours at room temperature. It was concentrated to dryness, eliminating the solvent at reduced pressure. The residue was dissolved in 250 mL of chloroform and washed with 50 mL of water. The organic phase was separated and washed with 3×50.0 mL of water.

After drying over anhydrous magnesium sulfate, it was filtered and the solvent eliminated at reduced pressure. After drying at reduced pressure, this results in 0.68 g of a white solid corresponding to the product of interest. Yield: 76%.

$^1$H-NMR (200 MHz, CDCl$_3$): 5.34-5.26 (1H, m, CHONO$_2$), 4.93 (1H, t, J=5.2 Hz, CHCHONO$_2$), 4.48 (1H, d, J=4.8 Hz, CHCHS), 4.14 (1H, dd, J=9.7 Hz, J=4.8 Hz, H—CHCHS), 4.01 (1H, dd, J=11.2 Hz, J=3.0 Hz, H—CHCHONO$_2$), 4.01-3.81 (2H, cs, H—CHCHS, H—CHCHONO$_2$), 3.30-3.24 (1H, m, CHS), 2.15 (3H, s, CH$_3$).

$^{13}$C-NMR (50 MHz, CDCl$_3$): 88.65 (CHCHS), 81.55 (CHCHONO$_2$), 81.26 (CHONO$_2$), 73.87 (CH$_2$CHS), 69.10 (CH$_2$CHONO$_2$) 50.74 (CHS), 14.74 (CH$_3$).

Example 4

Method to Obtain 2-[(R)-methylsulfinyl]isosorbide 5-mononitrate (4) and 2-[(S)-methylsulfinyl]isosorbide 5-mononitrate (4bis)

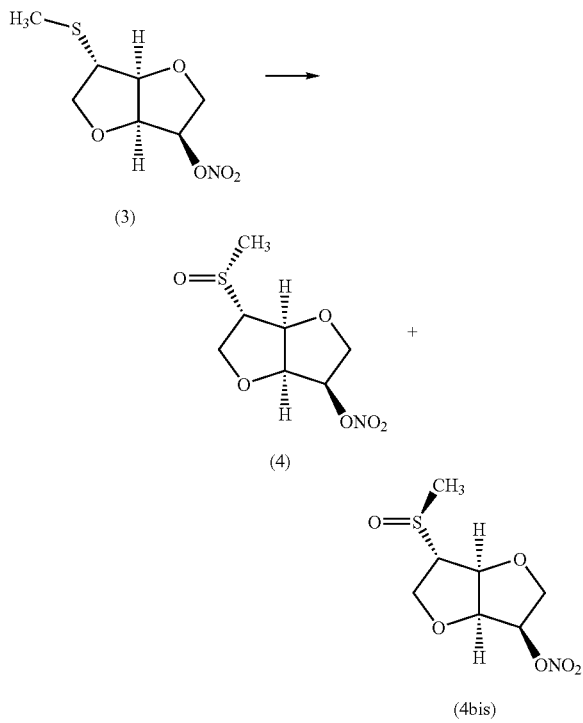

In a 500 mL flask, it was dissolved 7.3 g (32.9 mmol) of 2-methylthioisosorbide 5-mononitrate (3) obtained according to Example 3 in 75 mL of dioxane. A solution of 7.04 g (32.9 mmol) of NaIO$_4$ in 110 mL of water was added very slowly, drop by drop, and then stirred for 1 hour at room temperature. The mixture was filtered and then the dioxane was eliminated from the filtrate at reduced pressure. 150 mL of water were added. The mixture was extracted with 2×300 mL portions of chloroform. it was dried over anhydrous magnesium sulfate, filtered and the solvent eliminated at reduced pressure. This results in 6.6 g of a reaction crude containing a mixture of diastereoisomers in a proportion of 65% of (4) and 35% of (4bis). The resulting reaction crude was recrystallized from dioxane twice to obtain 2.9 g of the product of interest (4) with a purity of 95% by HPLC. Using the mother liquors from the first recrystallization, the solvent was eliminated at reduced pressure and the resulting residue recrystallized from dioxane to obtain 1 g of the product of interest (4bis) with a purity of 95% by HPLC.

2-[(R)-methylsulfinyl]isosorbide 5-mononitrate (4)

$^1$H-NMR (200 MHz, CDCl$_3$): 5.39-5.28 (1H, m, CHONO$_2$), 5.02 (1H, dd, J=5.6 Hz, J=1.6 Hz, CHCHS), 4.89 (1H, t, J=5.5 Hz, CHCHONO$_2$), 4.29 (1H, dd, J=10.4 Hz, J=6.4 Hz, H—CHCHS), 4.20-3.91 (3H, cs, H—CHCHS, CH$_2$CHONO$_2$), 3.38-3.31 (1H, m, CHSO), 2.61 (3H, s, CH$_3$).

$^{13}$C-NMR (50 MHz, CDCl$_3$): 82.11 (CHCHONO$_2$), 81.51 (CHCHS), 80.55 (CHONO$_2$), 69.65 (CH$_2$CHS) 69.28 (CH$_2$CHONO$_2$), 66.24 (CHSO), 37.28 (CH$_3$).

Microanalysis calculated (%): 35.44; C; 4.67; H, 5.90; N, 13.51; S, 40.47; O.

experimental (%): 35.31; C, 4.67; H, 5.98; N, 13.5; S, 40.60; O.

Mass Spectrometry (LC-(ApcI)MS to 20V): 238 (M+1)$^+$

Melting Point: 153° C. by DSC

Monocrystal X-Ray Diffraction: The configuration of the diasteromer (4) is establish as: (R)-S, (S)-C2, (S)-C3, (S)-C4, (R)-C5

2-[(S)-methylsulfinyl]isosorbide 5-mononitrate (4bis):

$^1$H-NMR (200 MHz, CDCl$_3$): 5.39-5.28 (1H, m, CHONO$_2$), 4.89 (1H, t, J=5.6 Hz, CHCHONO$_2$), 4.68 (1H, d, 5.4 Hz, CHCHS), 4.40-3.88 (4H, cs, CH$_2$CHS, CH$_2$CHONO$_2$), 3.48-3.40 (1H, m, CHSO), 2.58 (3H, s, CH$_3$).

$^{13}$C-NMR (50 MHz, CDCl$_3$): 82.89 (CHCHS), 82.26 (CHCHONO$_2$), 80.55 (CHONO$_2$), 69.19 (CH$_2$CHONO$_2$), 67.88 (CH$_2$CHS), 66.94 (CHSO), 36.64 (CH$_3$).

Microanalysis calculated (%): 35.44; C, 4.67; H, 5.90; N, 13.51; S, 40.47; O.

experimental (%): 35.65; C, 4.66; H, 5.87; N, 13.56; S, 40.57; O.

Mass Spectrometry (LC-(ApcI)MS to 20V): 238 (M+H)$^+$

Melting Point: 115° C. by DSC

Monocrystal X-Ray Diffraction: The configuration of the diasteromer (4bis) is establish as: (S)-S, (S)-C2, (S)-C3, (S)-C4, (R)-C5

Example 5

Method to Obtain 2-methylsulfonylisosorbide 5-mononitrate (5)

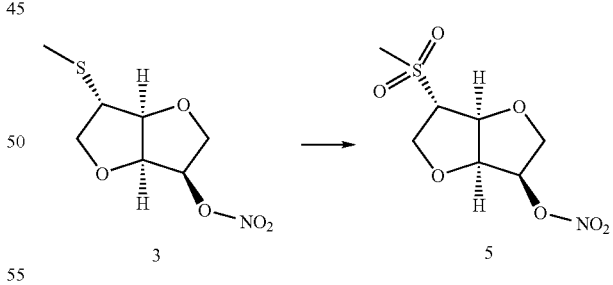

In a flask it was dissolved 1.0 g (4.5 mmol) of 2-methylthioisosorbide 5-mononitrate (3) obtained according to example 3 in 20 mL of acetonitrile. A solution of 4.11 g (18.1 mmol) of periodic acid (H$_5$IO$_6$) was added at once, and then stirred during 48 h at room temperature. 50 mL of a saturated solution of Na$_2$SO$_3$ are added. It is extracted with 2×30 mL of methylene chloride. The organic phases are united and they are washed with 2×30 mL of a saturated solution of Na$_2$SO$_3$. It was dried over anhydrous magnesium sulphate, filtered and the solvent eliminated at reduced pressure. 662 mg are obtained of the product of interest (5). 640 mg of the crude are suspended in 25 mL of hexane, filtered, and washed with 7.5 mL of chloroform, obtaining 450 mg of the product (5) with a purity of 99.7% by HPLC.

$^1$H-NMR (200 MHz, DMSO-$d_6$): 5.53-5.47 (1H, m, CHONO$_2$), 5.00-4.88 (2H, cs, CHCHONO$_2$, CHCHS), 4.38 (1H, dd, J=9.8 Hz, J=1.8 Hz, H—CHCHS), 4.12-3.86 (4H, cs, H—CHCHS, CH$_2$CHONO$_2$, CHSO$_2$), 3.07 (3H, s, CH$_3$).

$^{13}$C-NMR (50 MHz, DMSO-$d_6$): 82.77 (CHCHS), 82.36 (CHCHONO$_2$), 81.81 (CHONO$_2$), 68.95 (CH$_2$CHONO$_2$), 68.46 (CH$_2$CHS), 67.48 (CHSO$_2$), 39.31 (CH$_3$).

Microanalysis calculated (%): 33.20; C, 4.38; H, 5.53; N, 12.66; S, 44.23; O.

experimental (%): 33.45; C, 4.34; H, 5.52; N, 12.69; S, 44.43; O.

Mass Spectrometry (LC-(ApcI)MS to 20V): 254 (M+H)$^+$

Melting Point: 173° C. by DSC

Example 6

Method to Obtain S-nitroso-2-thioisosorbide 5-mononitrate (6)

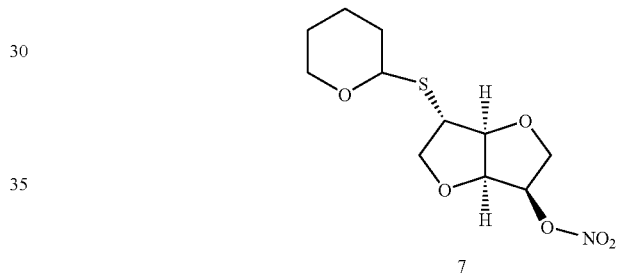

In an amber vial, 0.5 g (2.41 mmol) of 2-thioisosorbide 5-mononitrate (1) obtained according to Example 1 were dissolved in 4.0 mL of MeOH, covered and stirred in an ice bath. 320 µL (0.249 g, 2.41 mmol) of tert-butoxynitrite were added and stirred while covered and under cold conditions for 7 hours. The white solid was filtered off and the filtrate was concentrated to dryness at reduced pressure protected from exposure to light and at room temperature. This results in 0.48 g (yield: 84%) of a deep red solid identified as S-nitroso-2-thioisosorbide 5-mononitrate (6).

$^1$H-NMR (CDCl$_3$, 200 MHz): 5.40-5.25 (sc, 1H, CHONO$_2$), 4.84-4.64 (sc, 2H, CHSNO, CHCHONO$_2$), 4.40-4.30 (m, 2H, H—CHCHSNO, CHCHSNO), 4.12 (dd, 1H, J=11.4 Hz, J=2.6 Hz, H—CHCHONO$_2$) 4.00-3.80 (sc, 2H, H—CHCHSNO, H—CHCHONO$_2$).

$^{13}$C-NM (CDCl$_3$, 50 MHz): 88.2 (CHCHSNO), 81.9+81.1 (CHCHONO$_2$, CHONO$_2$), 73.4 (CH$_2$CHSNO), 69.5 (CH$_2$CHONO$_2$), 51.6 (CHSNO).

Example 7

Method to Obtain 2-(tetrahydropyran-2-yl-thio)isosorbide 5-mononitrate (7)

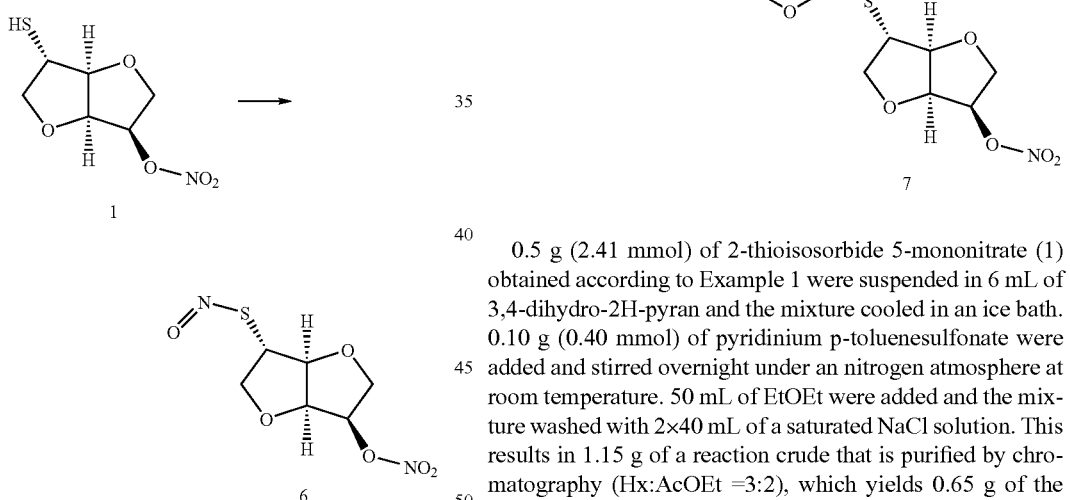

0.5 g (2.41 mmol) of 2-thioisosorbide 5-mononitrate (1) obtained according to Example 1 were suspended in 6 mL of 3,4-dihydro-2H-pyran and the mixture cooled in an ice bath. 0.10 g (0.40 mmol) of pyridinium p-toluenesulfonate were added and stirred overnight under an nitrogen atmosphere at room temperature. 50 mL of EtOEt were added and the mixture washed with 2×40 mL of a saturated NaCl solution. This results in 1.15 g of a reaction crude that is purified by chromatography (Hx:AcOEt =3:2), which yields 0.65 g of the product of interest with a purity of 83%. Recrystallization from hexane gave 0.45 g of the product with a purity of 95%, identified by its spectroscopy data as 2-(tetrahydropyran-2-yl)-2-thioisosorbide 5-mononitrate (7)

$^1$H-NMR (CDCl$_3$, 200 MHz): 5.28 (ddd, 1H, J=11.0 Hz, 5.4 Hz, 2.8 Hz, CHONO$_2$), 5.0-4.85 (sc, 2H, CHSTHP, CHCHONO$_2$), 4.59 (dd, 1H, J=11.2 Hz, 4.6 Hz, CHCH-STHP), 4.20-3.80 (sc, 5H, CH$_2$CHSTHP, H—CHCHONO$_2$, CH$_2$ $_{THP}$), 3.60-3.40 (sc, 2H, H—CHCHONO$_2$, CH$_{THP}$), 2.00-1.45 (sc, 6H, 3CH$_2$ $_{THP}$).

$^{13}$C-NMR (CDCl$_3$, 50 MHz): 89.5 and 89.1 (CHCHS), 83.0 and 81.6 (CHCHONO$_2$), 81.4 and 81.3 (CHSTHP, CHONO$_2$), 74.9 and 74.1 (CH$_2$ $_{THP}$), 69.0 and 68.9 (CH$_2$CHSTHP), 64.8 and 64.7 (CH$_2$CHONO$_2$), 49.1 and 47.6 (CH$_2$ $_{THP}$), 31.3 and 31.2 (CH$_2$ $_{THP}$), 25.4 (CH$_2$ $_{THP}$), 21.7 and 21.6 (CH$_2$ $_{THP}$).

Example 8

Method to Obtain 2-(isosorbidyl-2'-dithio)isosorbide 5-mononitrate (8)

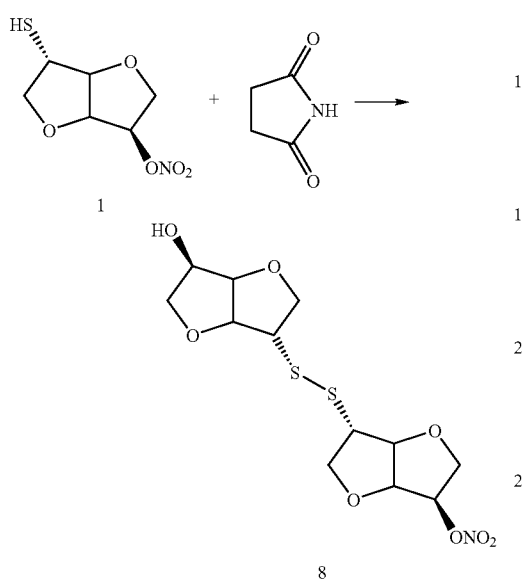

A solution of 0.170 g (1.72 mmol) of succinimide in EtOH was added to 0.323 g (1.56 mmol) of 2-thioisosorbide 5-mononitrate (1). After a white precipitate appears, 0.168 mg (2 mmol) of $NaHCO_3$ were added. After stirring at room temperature for 3 hours and 45 minutes an additional 100 mg (1.19 mmol) of $NaHCO_3$ and 10 drops of water were added. After an additional 1 hour and 30 minutes of stirring, the mixture was brought to reflux. After two hours at reflux, the EtOH was eliminated at reduced pressure; 150 mL of water and 150 mL of AcOEt were added. An emulsion is formed and $NaCl_{(s)}$ is added until the two phases are separated. The organic phase is separated and the aqueous phase washed with 2×150 mL portions of AcOEt. Each of the three organic phases is washed separately with 100 mL of water and the organic phases are combined and dried over anhydrous $Na_2SO_4$. This is filtered, washed with AcOEt and the solvent eliminated from the filtrate at reduced pressure, obtaining 336 mg of a reaction crude on which flash chromatography is performed. Use of a mixture of 1:1 $CHCl_3$/AcOEt as an eluent for the chromatographic separation results in a fraction of 98 mg of the product of interest (8).

$^1$H-NMR (300 MHz, $CDCl_3$): 5.40-5.32 (1H, cs, $CHONO_2$), 5.04-4.98 (1H, cs, $CHCHONO_2$), 4.70-4.60 (3H, cs, 3CH), 4.36-4.26 (1H, cs, CHOH), 4.22-4.12 (2H, cs, 2H—CH), 4.10-4.00 (3H, cs, 3H—CH), 3.94-3.86 (2H, cs, 2H—CH), 3.68-3.56 (3H, cs, 2CH—S, 1H—CH), 2.55 (1H, d, J=6.9 Hz, OH).

Infrared spectroscopy (in KBr pellet): 3461 $cm^{-1}$, 2987 $cm^{-1}$, 1642 $cm^{-1}$, 1465 $cm^{-}$, 1279 $cm^{-}$, 1077 $cm^{-}$, 846 $cm^{-1}$.

Microanalysis:
experimental (%): 39.53; C, 34.70; H, 4.77; O, 3.96; N, 17.04; S.
calculated(%): 39.23; C, 34.84; H, 4.66; O, 3.81; N, 17.45; S.

Mass spectrometry:
Electrospray: 368(M+1).

Electron impact (m/z, (% relative abundance)): 367 (7.4) (M+), 261 (3.8), 160 (8.6), 129 (15.5), 127(14.2), 85 (35.7), 69 (100).

Example 9

Step 1

Method to Obtain 2-thioisosorbide (9) and 2,2'-dithiodiisosorbide (10)

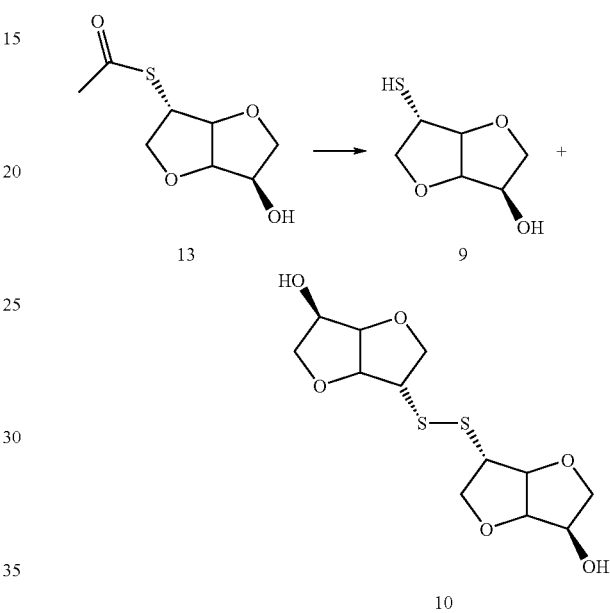

In a 500 mL flask, 15 g (74 mmol) of 2-acetylthioisosorbide (13) obtained according to WO 00/20420 are dissolved in 225 mL of EtOH. A 85% solution of 11.3 g of KOH in 150 mL of water is added. The resulting mixture is stirred at room temperature for 2 hours, neutralized with $ACOH_{(c)}$ and the EtOH eliminated at reduced pressure. The resulting solution is brought to basic pH by adding $NaOH_{(s)}$, and stirred at room temperature while bubbling an air stream through the solution for 10 hours. The solution is acidified with $HCl_{(c)}$ and brought to pH=4. The water is eliminated at reduced pressure and the resulting residue redissolved in $CH_2Cl_2$, filtered and dried over anhydrous $Na_2SO_4$. The solution is filtered, washed and the solvent eliminated from the filtrate at reduced pressure, obtaining 9.22 g of a reaction crude which is purified by flash chromatography using different mixtures of cyclohexane/ethyl acetate as eluent. The elution is started with 3 L of a 1:1 mixture, and after that, the percentage of the polar solvent increased, first with 2 L of a 3:5 mixture, later with 2 L of a 1:2 mixture and finally eluted only with AcOEt. A 2.64 g fraction of the thiol (9) and another 3.06 g of the disulfide (10) are isolated from the eluate.

2-Thioisosorbide (9)

$^1$H-NMR (200 MHz, $CDCl_3$): 4.68-4.58 (1H, cs, CHCHOH), 4.48-4.40 (1H, cs, CHCHSH), 4.34-4.18 (1H, bs, s.a. $D_2O$, CHOH), 4.16-4.06 (1H, m H—CHCHSH), 3.96-3.78 (2H, Cs, H—CHCHOH, H—CHCHSH), 3.62-3.50 (1H, cs, 1 H—CHCHOH), 3.48-3.36 (1H, cs, s.a. D$_2$O, CHS), 2.80-2.60 (1H, bs, d.a. D$_2$O, OH), 1.75 (1H, d, J=8 Hz, d.a. D$_2$O, SH).

$^{13}$C-NMR (50 Mz, CDCl$_3$): 90.42 (CHCHSH), 81.47 (CHCHOH), 76.27 (CH$_2$CHSH), 74.00 (CH$_2$CHOH), 72.04 (CHOH), 43.81 (CHSH).

2,2'-Dithiodiisosorbide (10)

$^1$H-NMR (200 MHz, CDCl$_3$): 4.68-4.56 (4H, cs, 2CHCHS, 2CHCHOH), 4.34-4.19 (2H, cs, s.a. D$_2$O, 2 CHOH), 4.19-3.97 (4H, cs, 2CH$_2$CHS), 3.92-3.80 (2H, cs, 2H—CHCHOH), 3.66-3.52 (4H, cs, 2H—CHCHOH, 2CHS), 2.63 (2H, d, J=6.6 Hz, d.a. D$_2$O, 2OH).

$^{13}$C-NMR (50 MHz, CDCl$_3$): 87.42 (2CHCHS), 81.98 (2CHCHOH), 73.93 (2CH$_2$CHOH) 72.89 (2CH$_2$CHS), 72.07 (2CHOH), 54.74 (2CHS).

Step 2

Method to Obtain 5,5'-diacetyloxy-2,2'-dithiodiisosorbide (14) and 2-(5'-acetyloxyisosorbidyl-2'-dithio) isosorbide 5-mononitrate (11)

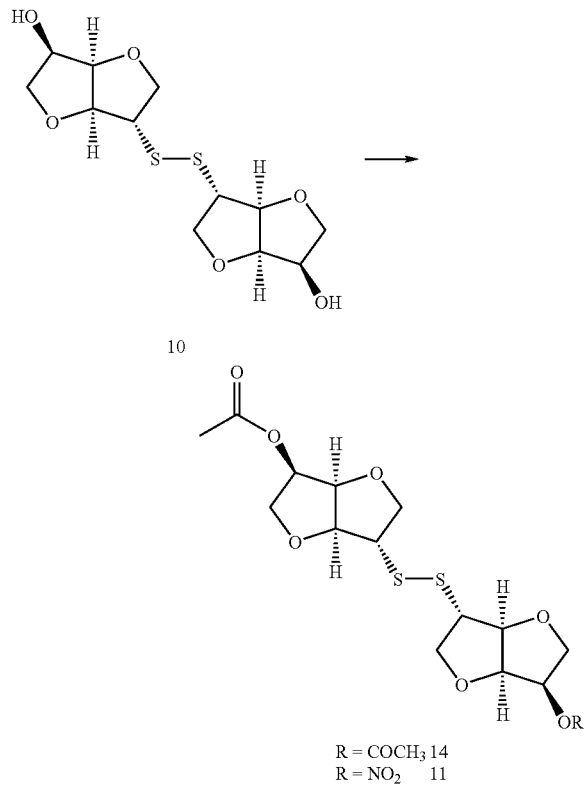

R = COCH$_3$ 14
R = NO$_2$ 11

A nitrating mixture is prepared by adding, slowly and with caution at 0° C., 1.8 mL of 60% HNO$_3$ to a mixture of 7.5 mL of acetic anhydride and 12.5 mL of acetic acid. In a 100 mL flask fitted with reflux cooler, thermometer and magnetic stirrer, 2.77 g (8.6 mmol) of 2,2'-dithio-diisosorbide (10) obtained according to Example 8 are dissolved in 17 mL of acetic acid and 3.5 mL of acetic anhydride are added. The mixture is cooled at 0° C. in an ice/salt bath. 4 mL of the previously prepared nitrating mixture is added dropwise over 15 minutes. It is stirred at 0° C. for 2 hours, observing the solidification of the reaction crude. Then it is stirred for 2 hours and 30 minutes at room temperature. The reaction crude is poured over 100 mL of water, filtered and washed with plenty of water. The resulting solid is dried at reduced pressure in the presence of P$_2$O$_5$. This results in 2.69 g of a reaction crude which is purified by preparative reversed phase chromatography. A 1:1-mixture of acetonitrile:water is used as an eluent for the chromatography. A 1.01 g fraction of the diacetate (14) (R=COCH$_3$) and another 0.5 g fraction of acetate-nitrate (11) (R=NO$_2$) is isolated.

5,5'-diacetyloxy-2,2'-dithiodiisosorbide (R=COCH$_3$) (14)

$^1$H-NMR (200 MHz, CDCl$_3$): 5.16-5.02 (2H, cs, 2CHOCO), 4.85-4.76 (2H, cs, 2CH—O—C), 4.63-4.56 (2H, cs, 2CHOC), 4.17-4.05 (2H, cs, 2H—CH), 4.00-3.74 (6H, cs, 6 H—CH), 3.56-3.48 (2H, cs, 2CHS), 2.09 (6H, s, CH$_3$).

$^{13}$C-NMR (50 MHz, CDCl$_3$): 170.27 (2CO), 87.73 (2CHCHS), 80.76 (2CHCHO), 73.79 (2CHO), 72.66 (2CH$_2$CHS), 70.46 (2CH$_2$CHO), 54.42 (2CHS), 20.63 (2CH$_3$).

2-(5'-Acetyloxyisosorbidyl-2'-dithio)-isosorbide 5-mononitrate (R=NO$_2$) (11)

$^1$H-NM (200 MHz, CDCl$_3$): 5.37-5.28 (1H, cs, CHONO$_2$), 5.18-5.06 (1H, cs, CHOCO), 5.02-4.94 (1H, cs, CHOC), 4.87-4.78 (1H, cs, CHOC), 4.64-4.56 (2H, cs, 2 CHOC), 4.18-3.75 (8H, cs, 4CH$_2$), 3.59-3.50 (2H, cs, 2 CHS), 2.10 (3H, s, CH$_3$).

$^{13}$C-NMR (50 MHz, CDCl$_3$): 170.29 (CO), 88.25 (CH), 87.43 (CH), 81.58 (CH), 81.16 (CH), 80.79 (CH), 73.80 (CH), 72.78 (CH$_2$), 72.66 (CH$_2$), 70.51 (CH$_2$), 69.32 (CH$_2$), 54.42 (CHS), 53.72 (CHS), 20.65 (CH$_3$).

Mass spectrometry:
Chemical ionization (NH$_3$): 410 (M+1)$^+$, 427 (M+18)$^+$.

Tests for Vasorelaxation

The method used in the assays is substantially the same as described in following references:

Furchgot, R. F., "Methods in nitric oxide research"; Feelisch & Stamler, eds., John Wiley & Sons, Chichester, England, pp 567-581.

Trongvanbichnam K., et al., Jpn. J. Pharmacol. 71 (1996); 167-173.

Salas, E., et al., Eur. J. Pharmacol. 258 (1994); 47-55.

The different compounds are tested at 5 different concentrations, at a concentration range from 0.0001 to 10 mM, using from 6 to 9 arterial rings for each compound. The obtained results are compared to those from the isosorbide 5-mononitrate, which is used as reference product.

The results are shown in table 1 below and are provided as EC$_{50}$ (effective concentration 50), which is the concentration of each of the tested-compounds yielding a vasodilatation equal to 50% of the maximum tone at which the artery ring has been contracted with 1 µM of Phenylephrine.

TABLE 1

Test of vasorelaxation

| Compound | EC$_{50}$ mM (mean ± s.d.) |
| --- | --- |
| Isosorbide 5-mononitrate | 0.92 ± 0.2 |
| (1) | 0.041 ± 0.006 |
| (2) | 0.0053 ± 0.001 |

TABLE 1-continued

Test of vasorelaxation

| Compound | $EC_{50}$ mM (mean ± s.d.) |
|---|---|
| (3) | 0.043 ± 0.006 |
| (4) | 0.338 ± 0.01 |
| (6) | 0.0012 ± 0.0001 |
| (7) | 0.05 ± 0.009 |
| (9) | 0.024 ± 0.005 |
| (12) | 0.023 ± 0.010 |

As it can be seen from the table, all the compounds tested are more potent as vasorelaxants than the reference product.

In Vitro Test of the Inhibition of the Platelet Aggregation

The method used in the assays is substantially the same as described in following reference:

Salas, E., et al., Br. J. Pharmacol. 112 (1994); 1071-1076.

The compounds are tested at four different concentrations, using platelet rich plasma from not less than 6 different healthy human donors. The results obtained are compared to those from 5-isosorbide mononitrate, which is used as reference product.

The results are shown in table 2 and are expressed as $IC_{50}$ (inhibitory concentration 50), which is the concentration of each of the tested compounds yielding an inhibition equal to 50% of the aggregation obtained with a submaximal concentration (1-4 µM) of ADP (a submaximal concentration of ADP is the minimal amount of ADP which produces the maximal aggregation).

TABLE 2

Test of inhibition of the aggregation of the platelets (Human Platelet Rich Plasma)

| Compound | $IC_{50}$ mM (mean ± s.d.) |
|---|---|
| Isosorbide 5-mononitrate | 2.68 ± 0.33 |
| (1) | 0.11 ± 0.01 |
| (2) | 0.01 ± 0.007 |
| (3) | 0.41 ± 0.09 |
| (4) | 1.00 ± 0.01 |
| (4bis) | 0.85 ± 0.15 |
| (6) | 0.0019 ± 0.0005 |
| (7) | 0.58 ± 0.021 |
| (12) | 0.089 ± 0.01 |

As can be seen from table 2, all the compound tested have a potent inhibitory activity on aggregation of the platelets, that is superior to that of the reference compound.

Inhibition of Human Monocyte and Platelet Adhesion to Human Endothelial Cells

The methods used in the assays to determine the effect of the compounds on platelet and monocyte adhesion to human endothelial cells are substantially the same as described in the following references:

Del Maschio A. et al., J Cell Biol 1996; 135: 497-510
Bombeli T. et al., Blood 1999; 93: 3831-3838
Colomé C. et al; Atherosclerosis 2000; 149: 295-302; and
Martin-Satue M. et al; British Journal of Cancer 1999; 80; 1169-1174

The adhesion of the U937-monocyte cells to confluent human microvasculature endothelial cells (HMEC-1) activated by means of TNF-α (50 ng/ml) and the platelets to human umbilical endothelial cells (HUVEC) were the methods used to determine the inhibitory effect of compounds on cellular adhesion. The adhesion of monocytes previously labeled with calcein-AM (Molecular Probes) to HMEC-1 activated by TNF-α, was assessed by determination of the associated-cell fluorescence. The adhesion of washed human platelets previously labeled with MoAb against CD36-FITC to activated-HUVEC (50 µg/ml of LDL minimally modified, LDLmm) was determined by Laser Scanning Cytometry (LSC, Olympus) determining the associated-cell fluorescence. Results are expressed as the percentage of inhibition respect to control (adhesion of the cells in the absence of compounds). Table 3 shows the effect of compounds on U937 adhesion to activated-HMEC-1. Table 4 shows the effect of compounds on platelet adhesion to activated HUVEC.

TABLE 3

Inhibition of U937 monocyte adhesion to activated HMEC-1 human endothelial cells

| Compound | % of inhibition to control (mean ± s.e.m.) |
|---|---|
| (1) | 30 ± 8 |
| (12) | 15 ± 2 |

TABLE 4

Inhibition of platelet adhesion to HUVEC activated by LDL mm (50 µg/ml)

| Compound | % of inhibition to control (mean ± s.e.m.) |
|---|---|
| (12) | 87.5% ± 5.1% |

Inhibition of LDL Transcytosis in Human Microvascular Endothelial Cells

The method used in the assays to determine the effect of the compounds on LDL transcytosis in human microvascular endothelial cells is substantially the same as described in Colomé C. et al; Atherosclerosis 2000; 149: 295-302. This test allows a prediction on the anti-atherosclerotic potential of the compounds, since the accumulation of LDL in the vascular wall as a consequence of a vascular endothelial cell active transport is one of the first steps in the development of atherosclerosis.

The method used in the assays to isolate LDL particles from fresh human plasma and the labelling with Dil is substantially the same as described in Pedreño J. et al., Atherosclerosis 2001; 155: 99-112, and Stephan Z. F. and Yuracheck E. C. J. Lipid Res. 1993; 34:325-330

Activated (100 µM histamine) and non activated HMEC-1 were cultivated in the upper well of inserted of coculture until to reach confluence (Falcon HTS FluorBloK). Then, LDL-Dil (up to 200 µg/ml) was added and cells were incubated for 2 h in the presence and absence of compounds. After these two hours, transcytosis of LDL-Dil particles through endothelial cells was assessed by determination of the presence of fluorescence in the lower well of insert of coculture. Results are expressed as percentage of inhibition respect to control (in the absence of compounds). Table 5 shows the effect of the compounds on the LDL-Dil transcytosis through HMEC-1.

TABLE 5

Inhibition of LDL transcytosis in human microvascular endothelial cells (% of inhibition to control (mean ± s.e.m.))

| Compound | Resting cells | Stimulated cells |
|---|---|---|
| (1) | 58 ± 15 | 122 ± 8 |
| (12) | 51 ± 19 | 80 ± 12 |

Inhibition of LDL Oxidation

The method used in the assays to determine the effect of the compounds on LDL oxidation is substantially the same as described in the following references:
Spranger T., et al., Chem. Phys. Lipids 1998; 91:39-52
Lynch S. M., et al., Biochim. Biophys. Acta 2000; 1485:11-22
Pedreño J., et al., Thromb. Res. 2000; 99: 51-60.

The method used in the assays to isolate LDL particles from fresh human plasma is substantially the same as described in Pedreño J., et al., Atherosclerosis 2001; 155: 99-112.

Oxidative modification of low-density lipoprotein (LDL) is currently believed to be a central event in the development of atherosclerotic cardiovascular disease. The exposition of LDL to globin-free haemin (the complex of ferric ion ($Fe^{3+}$) with protoporphyrin IX), derived from the haemoglobin in circulating erythrocytes, serves as a physiological source of pro-oxidant $Fe^{3+}$ capable to promoting LDL oxidation. The compounds were added in vitro to determine their inhibitory activity on LDL oxidation induced by haemin and $H_2O_2$. LDL at a final protein concentration of 0.2 mg/ml was incubated in the presence of 2.5 μm haemin and 5 μm $H_2O_2$. Oxidative modification of LDL particles was assessed by measurement of conjugated dienes. Experimental samples were incubated at 37° C. and the increase in absorbance at 234 nm was automatically recorded every 5 min for at least 5 h. The effect of compounds on the LDL oxidation induced by haemin was tested at 7 different concentrations using LDL preparations from 7 different healthy donors. Table 6 shows the inhibitory activity of the compounds at 10 μM expressed as the percentage of increase of lag phase (time that is required so that the reaction of formation of conjugate dienos begins) with respect to control.

TABLE 6

Inhibition of LDL oxidation

| Compound | % of increment of lag phase with respect to control (mean ± s.e.m.) |
|---|---|
| Isosorbide 5-mononitrate | 0 |
| (1) | 290 ± 8 |
| (12) | 117 ± 56 |

Inhibition of Plasma Oxidation

The method used in the assays to determine the effect of compounds on the capacity of oxidation of the plasma is substantially the same as described in Spranger T. et al., Chem Phys Lipids 1998; 91: 39-52.

Lipoprotein oxidation induced in vitro in plasma is expected to represent a relevant model of the lipoprotein oxidation in the arterial wall. Oxidation of plasma lipoproteins was assessed as the capacity of oxidation of heparinized plasma and was measured by spectrophotometry as in increase in absorbance at 234 nm. The compounds were added in vitro to determine their inhibitory activity over the capacity of oxidation of plasma induced by $Cu^{2+}$ ($CuSO_4$). Heparinized plasma was diluted with phosphate-buffered saline solution (PBS) containing 0.16 M NaCl and the oxidation was started by 50 μM $CuSO_4$. Experimental samples were incubated at 37° C. and the increase in absorbance at 234 nm was automatically recorded every 15 min for at least 12 h. The effect of compounds over the capacity of oxidation of plasma induced by $Cu^{2+}$ was tested at 7 different concentrations using heparinizaded plasma from 7 different healthy donors. Table 7 shows the inhibitory activity of the compounds at 10 μM expressed as the percentage of increase of lag phase with respect to control.

TABLE 7

Inhibition of plasma oxidation

| Compound | % of increment of lag phase with respect to control (mean ± s.e.m.) |
|---|---|
| (1) | 245 ± 26 |
| (2) | 7 ± 1 |
| (12) | 200 ± 10 |
| Isosorbide 5-mononitrate | 0 |

Preventive and Curative Effect on Atherogenesis in Rabbits Fed on High Cholesterol Diet The method used is substantially the same as described in Shore B, Shore V., In: Day CE (ed) Atherosclerosis Drug Discovery, Plenum Press, New York and London, pp 123-141, 1976.

Twenty-one male New Zealand White rabbits (10 weeks old at the beginning of the protocol) were maintained under standardized conditions (22° C., 40% to 60% humidity) with regular day/night cycle and free access to water. The animals were randomly assigned to 1 of 3 groups. Group 1 (n=5) received standard maintenance diet for 75 days; group 2 (n=16) received the same diet but supplemented with 1% (wt/wt) cholesterol for 45 days. At the end of this period, group 2 was classified into two randomly groups. The treated-group (n=9) receiving for additional 30 days 1.9 mg/kg/day of compound 12 (maintaining the 1% cholesterol in its diet), and the non-treated group (n=7) receiving a diet with a 1% of cholesterol for additional 30 days.

Study variables included triglycerides and total cholesterol. Animals were euthanized on day 75 after the start of the protocol with pentobarbital i.v. The entire aorta was removed 1 or 2 cm into the iliac arteries and fixed in buffer phosphate 0.1 M (pH 7.4) with glutaraldehyde (4%). Macroscopic and microscopic analyses of the samples were performed in a blinded fashion. Aortas were dissected and stained with Red Oil. Adventitial fat was removed, and aortas were opened longitudinally, immersed in Red Oil solution for overnight, washed in propylenglycol and fixed onto a flat surface. Images of the aortas were taken with a standard camera. Subsequently, 3 sections were taken from the aortic arch area, the thoracic aorta, and at the abdominal aorta (renal orifices). Sections were paraffin-embedded, were cut with a microtome Ultracut (Spain) and stained conventionally with hematosiline eosin. Images of aortas stained with Red Oil and hematosiline eosin were taken with a standard camera. Images were imported into Photoshop (Adobe) with a AGFA slide scanner. By means of the procedure previously described by Lillie R D (Lillie, R. D., 1994, Stain Technology, vol. 19, pp 55) the surface of injury in all the aorta and the thickness of the intima in histological samples was determined. The surface or area of the atherosclerotic injury (evaluated from the stained aortas with the Red Oil) are determined by the number of pixels of the image turned to mm². The intima thickness of the arteria (evaluated from the stained histological samples with Haematosiline-Eosin) was quantified in mm in a similar way to that described the surface or area of the atherosclerotic injury. For it, the sections that contained injuries of fatty striae were selected and the thickness of the intima was determined (from the arterial media to endothelium). The mean thickness of the lesion area was assessed in representative sections per aortic quadrant, and the statistical mean was calculated. The fasting plasmatic total cholesterol, HDL cholesterol and triglycerides levels are shown in table 8. The statistical examination (Student t) has revealed no significant difference between the medicated group and the control group (the group not medicated but with high cholesterol diet) in regard to plasma lipid.

TABLE 8

Plasmatic lipid profile [mg/dl] (mean ± s.e.m.)

|  | Control | | Treated with the compound example (12) | |
|---|---|---|---|---|
|  | Basal | End | Basal | End |
| Total cholesterol | 42 ± 4.4 | 1073.9 ± 4.9 | 33.3 ± 4.1 | 1461 ± 147 |
| Triglycerides | 185 ± 50 | 312.7 ± 130 | 121 ± 34 | 347 ± 82 |

The area rate covered by the atherosclerotic lesions are shown in table 9.

TABLE 9

Atherosclerotic lesions

| Group | Area percent of atherosclerotic lesions (%) (mean ± s.e.m.) |
|---|---|
| Control | 62 ± 6 |
| Treated with the compound example (12) | 15 ± 3 |

The thickness of intimal layer of the aorta is shown in table 10.

TABLE 10

Thickness of the intimal layer of the aorta

| Group | Thickness mm (mean ± s.e.m.) |
|---|---|
| Control | 0.323 ± 0.013 |
| Treated with the compound example (12) | 0.096 ± 0.009 |

In table 8 it is shown that there was no difference in plasma lipids between the control and the medicated group thereby demonstrating that the compound (12) did not influence upon lipid metabolism. As seen in table 9 and in table 10, both area percent of the atherosclerotic lesions as the intimal thickness were significantly reduced in the group treated with the compound (12) in comparison with the control group.

Preventive and Curative Effect on Atherogenesis in apo E-Deficient Mouse

The preventive and therapeutic effect of the present compounds on atherosclerosis will be also illustrated by way of the following example.

Preventing and curative effect on atherogenesis of the compounds it is investigated in apo E-deficient mouse fed on standard diet model. Male and female apo E-deficient mouse (OLA129X C57/BL6J) of three months old were fed on standard diet. The control group included 8 males and 7 females mouse, while the treated group consist of 8 males and 7 females mouse. All the animals had similar cholesterol and body weight at the beginning of the experiment. Both the control and the treated groups were studied for 12 weeks. The treated group received 5 mg/Kg/day of the compound (12).

Plasma lipid parameters (total cholesterol, HDL cholesterol and triglycerides) and oxidative stress (measured as 8-iso-prostaglandin F2α levels) were measured at predetermined intervals. After completion of the administration period, the thoracic aorta was isolated and stained to determine the area of the atherosclerotic injuries deposited in the internal wall of the blood vessel in according with the Red Oil method (Lillie, R. D., 1994, Stain Technology, vol. 19, pp 55).

The fasting plasmatic levels of total cholesterol, HDL cholesterol, triglycerides and 8-iso-prostaglandin F2α levels are shown in table 11.

TABLE 11

Plasmatic lipids and oxidative stress parameters (mean ± s.d.)

|  | Male | | Female | |
|---|---|---|---|---|
|  | Control | Treated with compound (12) | Control | Treated with the compound (12) |
| Total cholesterol (mmol. L-1) | 14.3 ± 2 | 18 ± 3 | 9.5 ± 2 | 11.3 ± 1.5 |
| HDL-cholesterol (mmol. L-1) | 0.5 ± 0.15 | 0.47 ± 0.15 | 0.4 ± 0.1 | 0.48 ± 0.13 |
| Triglycerides (mmol. L-1) | 2.6 ± 0.6 | 1.5 ± 0.4 | 1.9 ± 0.6 | 1.3 ± 0.2 |
| 8-iso-prostaglandin F2α (pg. mL-1) | 273 ± 19 | 101 ± 13 | 182 ± 19 | 99 ± 7 |

The area rate covered by the atherosclerotic lesions on the inner wall of the blood vessel and the area covered with macrophages are shown in table 12.

TABLE 12

| Group | Area covered with macrophages [μm²] (mean ± s.e.m.) | Area of atherosclerotic lesions [μm²] (mean ± s.e.m.) |
|---|---|---|
| Control | 80 ± 27 | 60 ± 8 |
| Treated with the compound example (12) | 55 ± 19 | 45 ± 9 |

In table 11 it is shown that compound (12) is able to decrease the levels of triglycerides in plasma as well as the oxidative stress of those animals. In table 12 it is shown how the compound (12) reduces both the area of the atherosclerotic lesions and the area covered with macrophages.

In Vivo Antithrombotic Effect

The method used is substantially the same as described by Kurz (Kurz K. D., et al., Thromb. Res. 1990, 60:269-280) and modified by Feuerstein (Feuerstein G. Z., et al., Artherioscler. Thromb. Vasc. Biol. 1999, 19: 2554-25562).

Rats received a single oral dose of 100 mg/Kg of the compounds.

Forty-five minutes after dosing rats were anaesthetized with sodium pentobarbital (40 mg/kg, i.p.) and they were placed later dorsally on a heated (37° C.) surgical board.

The left carotid artery was isolated and a Parafilm M sheet (7×20 mm, American National Can) was placed under it. An electromagnetic sounding of flow (Transonic Systems Inc.) was placed on the artery to measure blood flow.

Sixty minutes after product administration, a paper patch saturated with FeCl$_3$ solution (70%) was placed (and not removed for the whole duration of the experiment) on the left carotid artery downstream from the sounding of flow to initiate thrombosis. The blood flow was controlled during the 60 min later to the application of the patch in the artery.

The vessel was considered totally occluded by the thrombus formed when no blood flow was detected (0.0 ml/min). In this model, thrombus formation usually takes place within 15 to 20 minutes in non-treated animals. An animal was considered as fully protected by treatment if a thrombus did not occlude the vessel during the period of study (60 min after FeCl$_3$ continue patch application).

The results are shown in table 13 and are expressed as percentage of animals fully protected by the treatment.

TABLE 13

In vivo anti-thrombotic activity

| Compound | % of animals fully protected |
|---|---|
| 1 | 100 |
| 3 | 100 |
| 4 | 80 |
| 12 | 71 |

As it can be observed in table 13, all the compound tested have a potent in vivo anti-thrombotic activity.

In Vivo Synergistic Antithrombotic Effect

The method used is substantially the same as described by Kurz (Kurz K. D., et al., Thromb. Res. 1990, 60: 269-280) and modified by Feuerstein (Feuerstein G. Z., et al., Artherioscler. Thromb. Vasc. Biol. 1999, 19: 2554-25562).

Rats received a single oral dose of one or the combination of two compounds as described in table 14. The doses of the compounds used did not modify the blood pressure nor the heart rate of the animals.

Forty-five minutes after dosing administration, rats were anaesthetized with sodium pentobarbital (40 mg/kg, i.p.) and they were placed later dorsally on a heated (37° C.) surgical board.

The left carotid artery was isolated and a Parafilm M sheet (7×20 mm, American National Can) was placed under it. An electromagnetic sounding of flow (Transonic Systems Inc.) was placed on the artery to measure blood flow.

Sixty minutes after product administration, a paper patch saturated with FeCl$_3$ solution (70%) was placed (and not removed for the whole duration of the experiment) on the left carotid artery downstream from the sounding of flow to initiate thrombosis. The blood flow was controlled during the 60 min later to the application of the patch in the artery.

The vessel was considered totally occluded by the thrombus formed when no blood flow was detected (0.0 ml/min). In this model, occlusive thrombus formation usually takes place within 15 to 20 minutes in non-treated animals. An animal was considered as fully protected by treatment if a thrombus did not occlude the vessel during the period of study (60 min after FeCl$_3$ continue patch application).

The fractional product concept was used to identify synergy between the compounds. In accordance with this concept, if we consider the full protection of the animal as:

$$\text{Fractional inhibition} = \left(1 - \frac{A}{B}\right) \times 100$$

where A is the rate of animals with thrombotic occlusion in treated group; and B is the rate of animals with thrombotic occlusion in the control group.

For two drugs that act of independent way:

$$\text{Fractional inhibition} = \left[1 - \left(\frac{A_1}{B} \times \frac{A_2}{B}\right)\right] \times 100$$

where $A_1$ is the rate of animals with thrombotic occlusion in the treatment group $A_1$; $A_2$ is the rate of animals with thrombotic occlusion in the treatment group $A_2$; and B is the rate of animals with thrombotic occlusion in the control group If the protection obtained with the combination of the drugs is higher than the fractional inhibition for two compounds acting independently then synergism is considered to occur.

The results are shown in table 14 and are expressed as rate of animals with thrombotic occlusion in each group.

TABLE 14

| Group | Rate of animals with thrombotic occlusion (% of animals protected) |
|---|---|
| Control | 1 (0%) |
| Acetyl salicylic acid (100 mg/Kg/day, oral, for 3 days) | 0.50 (50%) |
| Compound 12 (22.3 mg/Kg, oral, acute the day of study) | 0.5 (50%) |
| Acetyl salicylic acid (100 mg/Kg/day, oral for 3 days) + compound 12 (22.3 mg/Kg, oral, acute the day of study) | 0 (100%) |
| Clopidogrel (1.5 mg/Kg/day, oral for 3 days) | 0.50 (50%) |
| Clopidogrel (1.5 mg/Kg/day, oral for 3 days) + compound 12 (22.3 mg/Kg, oral, acute the day of study) | 0.17 (83%) |

$$\text{Fractional inhibition}_{\text{(acetyl salicylic acid + compound 12)}} = \left[1 - \left(\frac{0.5}{1} \times \frac{0.5}{1}\right)\right] \times 100 = 75\%$$

As the percentage of animals protected with the combination of the two drugs (acetyl salicylic acid+compound 12) is higher than 75% (it is 100%) there is a synergism between the two products.

$$\text{Fractional inhibition}\left(\begin{array}{c}\text{clopidogrel +} \\ \text{compound (12)}\end{array}\right) = \left[1 - \left(\frac{0.5}{1} \times \frac{0.5}{1}\right)\right] \times 100 = 75\%$$

As the percentage of animals protected with the combination of the two drugs (clopidogrel+compound 12) is higher than 75% (it is 83%) there is a synergism between the two products.

In Vitro Protection Against the Cytotoxicity Induced by Oxygen Radicals Using the XTT-Based Method in HUVEC Cells The method used is substantially the same as described by Caveda L., et al. (J. Clin. Invest. 1996; 98: 886-893).

For the determination of the capacity to inhibit the cytotoxicity induced by oxygen radicals Human Umbilical Vein Endothelial Cells (HUVEC) were used. HUVEC were isolated and cultured in M199 and 20% FCS (Fetal Calf Serum).

Test XTT assay is based on hydrolysis by the metabolically active cells of the salt of tetrazolio XTT to form an orange product, the formazan dye formed is soluble and is directly quantified using an spectrophotometer.

HUVEC cells were cultivated until a sub-confluence status in a 96 well tissue culture plate and pre-treated with 50 μM of the compound for one hour. After that, cells were treated with 800 μM of peroxynitrite for an overnight.

After overnight incubation cells were incubated with the yellow XTT solution (final concentration 0.3 mg/ml) for 4 hours. After this incubation period, orange formazan solution was formed, which was spectrophotometrically quantified using an ELISA plate reader at 450 nm The results are shown in table 15 and are expressed as percentage of death cells.

TABLE 15

| In vitro cytoprotective activity | |
|---|---|
| Compound | % of death cells |
| 1 | 80 |
| 2 | 80 |
| 3 | 80 |
| 12 | 50 |

As it can be observed in table 15, all the compound tested have a cell protective activity (P<0.05) against the cell damage induced by oxygen radicals.

In Vivo Protection Against Ischemia-Reperfusion Damage in the Heart

Experiments were performed according to the model previously described by Hirata Y et al (Journal of Cardiovascular Pharmacology. 1998, 31: 322-326)

After a food fasting period of 6 hours, animals were divided into groups of at least 8 animals each. Doses of products were given by oral sounding 1 h before the ischemia induction. Animals were anaesthetized with pentobarbital (40 mg/kg, i.p.) and the standard limb lead II electrocardiogram was recorded to detect the S-wave depression. 0.3 U/kg arginine-vasopressin (AVP)(Sigma Chemicals, St Louis, Mo., USA) was injected into the carotid artery to induce vasoconstriction of small coronary arteries and increase in coronary resistance. In all the groups received AVP 60 min after the test drug. In all groups, after AVP injection of 10 minutes ECG recording was performed.

The results are shown in table 16 and are expressed as S-wave decrements (μvolts).

TABLE 16

| Compound | dose (mg/kg, p.o.) | S-wave decrement (μV) | Protection of S-wave decrement (%) |
|---|---|---|---|
| Vehicle | — | 46.2 ± 4.9 | — |
| 12 | 20 | 22.6 ± 5.9 | 52 |
| 12 | 100 | 8.6 ± 2.8 | 81 |
| 9 | 20 | 16.5 ± 9.8 | 64 |
| 9 | 100 | 9.7 ± 4.6 | 79 |
| 4 | 20 | 36.5 ± 11.6 | 21 |
| 4 | 100 | 5.9 ± 3.9 | 87 |

As it can be observed in table 16, all the compounds tested protect against ischemia-reperfusion damage in the heart.

Scheme 1:

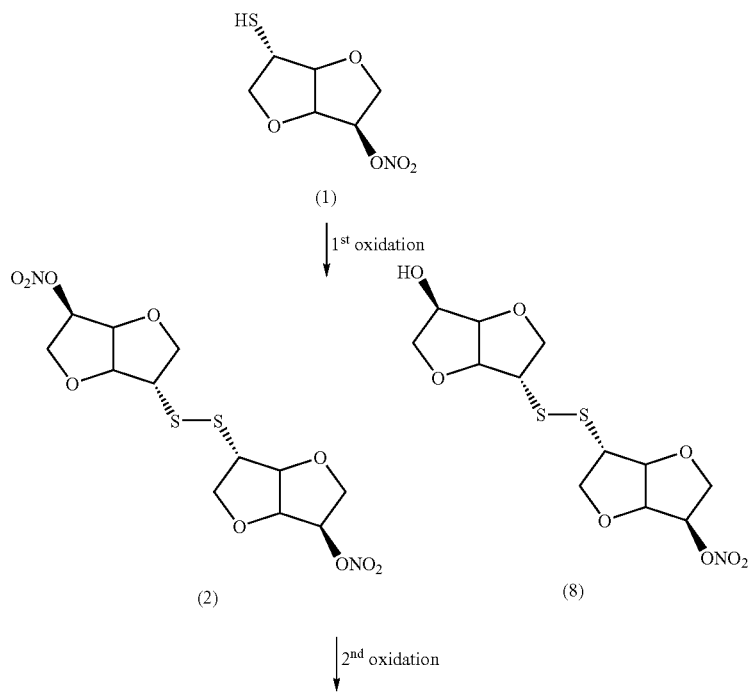

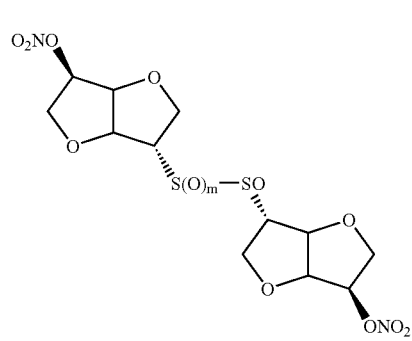
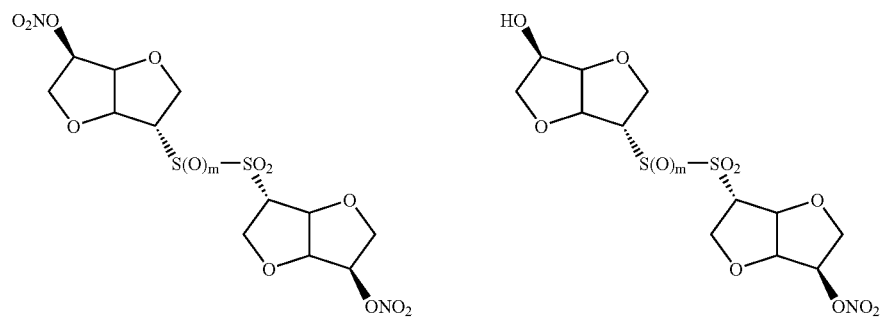
30
Scheme 2:
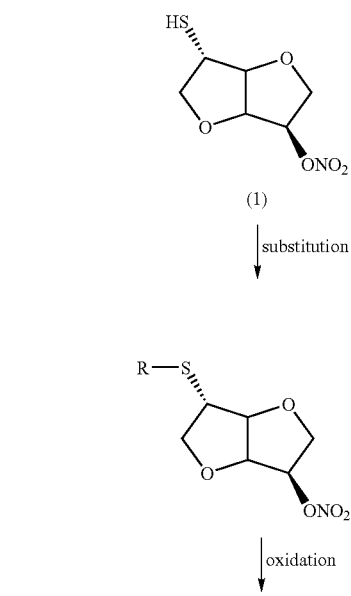
Scheme 3:
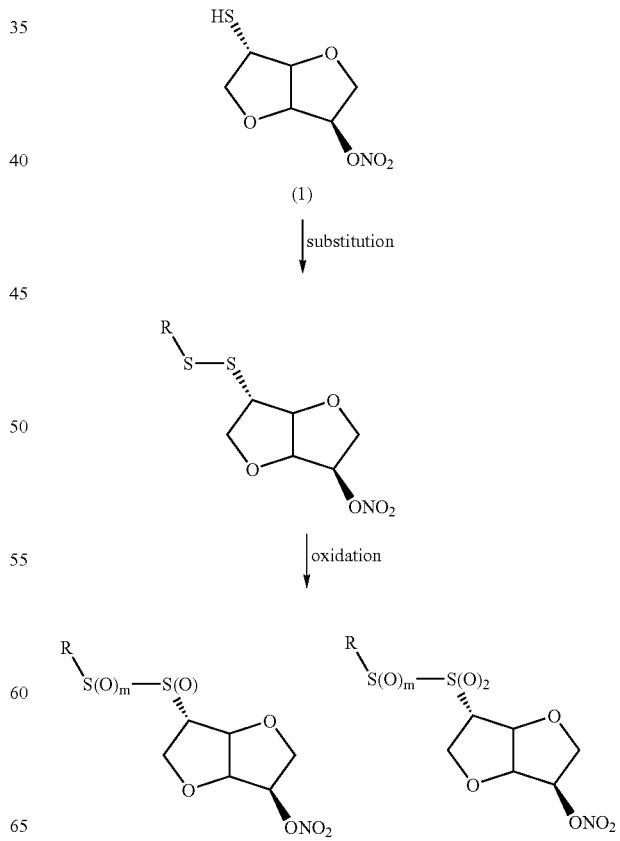

Scheme 4:

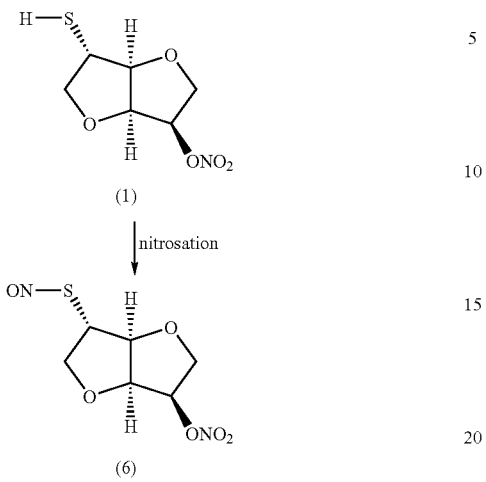

The invention claimed is:

1. A compound according to formula (I) or a a pharmaceutically acceptable salt, thereof:

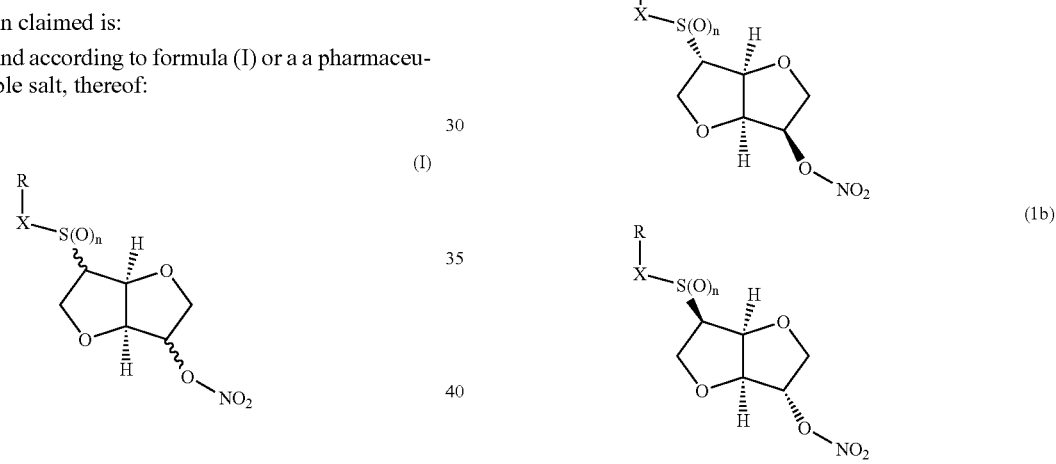

wherein:

n is an integer of 0, 1, or 2

X represents —S(O)$_m$—, —(C=O)— or a single bond, wherein m is an integer of 0, 1, or 2, with the proviso that when X represents —(C=O)—, then n is 0, R represents hydrogen or is a residue R$^a$, which residue R$^a$ is selected from the group consisting of:

C$_{1-6}$ alkyl;

C$_{2-6}$ alkenyl;

C$_{3-8}$ cycloalkyl;

C$_{3-8}$ cycloalkyl, wherein one CH$_2$ group is replaced by O, S, NH or NCH$_3$;

C$_{4-8}$ cycloalkenyl;

C$_{4-8}$ cycloalkenyl, wherein one CH$_2$ group is replaced by O, S, N or NCH$_3$;

phenyl;

pyridyl;

thiophenyl;

nitrosyl;

S-cysteinyl;

S-glutathionyl; and wherein R* is selected from the group consisting of hydrogen, C$_{1-6}$ alkyl, C$_{2-6}$ alkenyl, C$_{3-8}$ cycloalkyl; C$_{4-8}$ cycloalkenyl, acetyloxy, hydroxyl, ONO$_2$ and halogen, wherein R$^a$ optionally is substituted by one to three groups independently selected from C$_{1-6}$ alkyl, C$_{2-6}$ alkenyl, C$_{3-8}$ cycloalkyl, C$_{4-8}$ cycloalkenyl, acetyloxy, hydroxyl, ONO$_2$ and halogen, provided that when RXS(O)$_n$— and —ONO$_2$ are trans to each other with respect to the ring plane as depicted in formulae (Ia) and (Ib):

then RXS(O)$_n$— does not represent

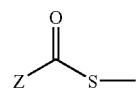

wherein Z is an C$_1$-C$_4$ alkyl group, aryl group, or an aralkyl group.

2. A compound according to claim 1, wherein either one or both of m and n is 0.

3. A compound according to claim 1, wherein X represents a single bond or —S—.

4. A compound according to claim 1, wherein R represents hydrogen, C$_{1-6}$ alkyl, C$_{2-6}$ alkenyl, C$_{3-8}$ cycloalkyl, C$_{4-8}$ cycloalkenyl, (C$_{1-6}$ alkyl) C$_{3-8}$ cycloalkyl, (C$_{1-6}$ alkyl) C$_{4-8}$ cycloalkenyl, phenyl, (C$_{1-6}$ alkyl)phenyl, 5-acetyloxyisosorbid-2-yl, 5-hydroxyisosorbid-2-yl or 5-nitratoisosorbid-2-yl.

5. A compound according to claim 1, wherein R is C$_{1-6}$ alkyl.

6. A compound according to claim 1, which is a compound according to formula (Ic) or Id):

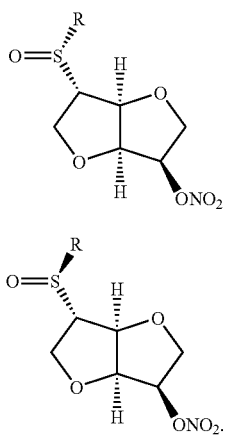

(1c)

(1d)

7. A compound according to claim 1, which is selected from:
2-thioisosorbide 5-mononitrate,
5,5'-dinitrate-2,2'-dithiodiisosorbide,
2-methylthioisosorbide 5-mononitrate,
2-[(R)-methylsulfinyl]isosorbide 5-mononitrate,
2-[(S)-methylsulfinyl]isosorbide 5-mononitrate
2-methylsulfinylisosorbide 5-mononitrate,
2-methylsulfonylisosorbide 5-mononitrate,
S-nitroso-2-thiososorbide 5-mononitrate,
2-(tetrahydropyran-2-yl-thio)isosorbide 5-monoitrate,
2-(isosorbidyl-2'dithio)isosorbide 5-mononitrate, and
2-(5'-acetyloxyisosorbidyl-2'-dithio)isosorbide 5-mononitrate.

8. A pharmaceutical composition comprising as active ingredients(s) at least one compound according to claim 1, optionally together with one or more physiologically acceptable excipient(s).

9. 2,2'-dithiodiisosorbide.

* * * * *